United States Patent
Huang et al.

(10) Patent No.: US 10,034,656 B2
(45) Date of Patent: Jul. 31, 2018

(54) SYSTEMS AND METHODS FOR INCREASING EFFICIENCY OF ULTRASOUND WAVEFORM TOMOGRAPHY

(71) Applicant: LOS ALAMOS NATIONAL SECURITY, LLC, Los Alamos, NM (US)

(72) Inventors: Lianjie Huang, Los Alamos, NM (US); Zhigang Zhang, Los Alamos, CA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 879 days.

(21) Appl. No.: 14/339,770

(22) Filed: Jul. 24, 2014

(65) Prior Publication Data

US 2014/0364737 A1    Dec. 11, 2014

Related U.S. Application Data

(63) Continuation of application No. PCT/US2013/024676, filed on Feb. 4, 2013.
(Continued)

(51) Int. Cl.
*A61B 8/13*  (2006.01)
*A61B 8/08*  (2006.01)
(Continued)

(52) U.S. Cl.
CPC .......... *A61B 8/5207* (2013.01); *A61B 5/0073* (2013.01); *A61B 5/7275* (2013.01); *A61B 8/085* (2013.01); *A61B 8/0825* (2013.01); *A61B 8/13* (2013.01); *A61B 8/14* (2013.01); *A61B 8/145* (2013.01); *A61B 8/15* (2013.01);
(Continued)

(58) Field of Classification Search
None
See application file for complete search history.

(56) References Cited

U.S. PATENT DOCUMENTS 4,075,883 A    2/1978   Glover
4,582,065 A    4/1986   Adams
(Continued)

FOREIGN PATENT DOCUMENTS

KR    1020100075011 A    7/2010
WO    2007133882 A2    11/2007
(Continued)

OTHER PUBLICATIONS

Margrave et al. ("Full Waveform Inversion with Wave Equation Migration and Well Control", CREWES Research Report vol. 22 (2010), pp. 1-20).*
(Continued)

*Primary Examiner* — Amanda Lauritzen Moher
*Assistant Examiner* — Farouk Bruce
(74) *Attorney, Agent, or Firm* — Lewis Roca Rothgerber Christie LLP

(57) ABSTRACT

Ultrasound tomography imaging methods for imaging a tissue medium with one or more ultrasound transducer arrays comprising a plurality of transducers, wherein said transducers comprise source transducers, receiving transducers. The methods include assigning a phase value or time delay to source transducers, exciting the transducers and calculating a search direction based on data relating to the excited transducers.

18 Claims, 26 Drawing Sheets

Related U.S. Application Data

(60) Provisional application No. 61/594,865, filed on Feb. 3, 2012.

(51) Int. Cl.

| | |
|---|---|
| *A61B 8/00* | (2006.01) |
| *A61B 8/14* | (2006.01) |
| *A61B 8/15* | (2006.01) |
| *G01S 15/89* | (2006.01) |
| *A61B 5/00* | (2006.01) |
| *G06T 5/00* | (2006.01) |
| *G06T 11/00* | (2006.01) |

(52) U.S. Cl.
CPC ............ *A61B 8/406* (2013.01); *A61B 8/4477* (2013.01); *A61B 8/4488* (2013.01); *A61B 8/4494* (2013.01); *A61B 8/483* (2013.01); *G01S 15/8915* (2013.01); *G01S 15/8929* (2013.01); *G01S 15/8997* (2013.01); *G06T 5/001* (2013.01); *G06T 11/005* (2013.01)

(56) References Cited

U.S. PATENT DOCUMENTS

| | | | |
|---|---|---|---|
| 5,465,722 | A | 11/1995 | Fort et al. |
| 5,908,390 | A | 6/1999 | Matsushima |
| 6,186,951 | B1 | 2/2001 | Lizzi et al. |
| 2001/0020130 | A1 | 9/2001 | Gee et al. |
| 2002/0099290 | A1 | 7/2002 | Haddad |
| 2002/0173722 | A1 | 11/2002 | Hoctor |
| 2003/0158481 | A1 | 8/2003 | Stotzka |
| 2004/0034307 | A1 | 2/2004 | Johnson et al. |
| 2005/0197576 | A1* | 9/2005 | Luo ...................... A61B 8/0875 600/438 |
| 2006/0058678 | A1 | 3/2006 | Vitek |
| 2006/0173304 | A1 | 8/2006 | Wang |
| 2006/0184020 | A1 | 8/2006 | Sumi |
| 2006/0293597 | A1 | 12/2006 | Johnson et al. |
| 2007/0100239 | A1 | 5/2007 | Nair et al. |
| 2008/0045864 | A1 | 2/2008 | Candy et al. |
| 2008/0081993 | A1 | 4/2008 | Waki |
| 2008/0229832 | A1 | 9/2008 | Huang |
| 2008/0294043 | A1* | 11/2008 | Johnson ............... A61B 8/0825 600/437 |
| 2008/0319318 | A1 | 12/2008 | Johnson et al. |
| 2009/0076389 | A1 | 3/2009 | Jin et al. |
| 2009/0099456 | A1 | 4/2009 | Burcher et al. |
| 2010/0157732 | A1 | 6/2010 | Saenger et al. |
| 2011/0118984 | A1 | 5/2011 | Chevion et al. |
| 2011/0125014 | A1 | 5/2011 | Derode et al. |
| 2011/0131020 | A1* | 6/2011 | Meng ..................... G01V 1/303 703/2 |

FOREIGN PATENT DOCUMENTS

| | | |
|---|---|---|
| WO | WO2007133882 A2 | 11/2007 |
| WO | 2011103303 A2 | 8/2011 |
| WO | WO2011103303 A2 | 8/2011 |

OTHER PUBLICATIONS

Boonyasiriwat et al. ("3D Multisource Full-Waveform Inversion using Dynamic Random Phase Encoding", Society of Exploration Geophysicists Technical Program Expanded Abstracts 2010. pp. 1044-1049).*
Sallard et al. ("Use of a priori Information for the Deconvolution of Ultrasonic Signals", Rev. of Prog. in Quantitative Nondestructive Evaluation, vol. 17 Plenum Press, New York, 1998, pp. 735-742).*
Cuiping, Li et al., "In Vivo Breast Sound-Speed Imaging with Ultrasound Tomography", Ultrasound in Medicine & Biology, Oct. 2009, vol. 35, No. 10, pp. 1616-1628.
Korean Intellectual Property Office (KIPO), International Search Report and Written Opinion dated Jun. 2, 2013, Counterpart PCT International Application No. PCT/US2013/024676, pp. 1-10, with claims searched, pp. 11-18.
Korean Intellectual Property Office (KIPO), International Search Report and Written Opinion dated May 30, 2013, PCT International Application No. PCT/US2013/024545, pp. 1-12, with claims searched, pp. 13-20.
Korean Intellectual Property Office (KIPO), International Search Report and Written Opinion dated May 30, 2013, PCT International Application No. PCT/US2013/024656, pp. 1-10, with claims searched, pp. 11-16.
Korean Intellectual Property Office (KIPO), International Search Report and Written Opinion dated May 30, 2013, PCT International Application No. PCT/US2013/024662, pp. 1-10, with claims searched, pp. 11-19.
Korean Intellectual Property Office (KIPO), International Search Report and Written Opinion dated May 30, 2013, PCT International Application No. PCT/US0213/024539, pp. 1-16, with claims searched, pp. 17-24.
Office action dated May 9, 2017 issued in co-pending U.S. Appl. No. 14/339,780.
Office action dated Mar. 31, 2017 issued in co-pending U.S. Appl. No. 14/339,712.
Office action dated Apr. 4, 2017 issued in co-pending U.S. Appl. No. 14/339,738.
Office action dated May 10, 2017 issued in co-pending U.S. Appl. No. 14/339,791.
Office action dated May 2, 2017 issued in co-pending U.S. Appl. No. 14/339,728.
Office action dated May 1, 2017 issued in co-pending U.S. Appl. No. 14/339,759.
Anagaw et al., "Full Waveform Inversion with Total Variation Regularization," Recovery—2011 CSPG CSEG OWLS Convention, pp. 1-4.
Cobbold, (2007), Foundations of Biomedical Ultrasound, New York: Oxford University Press, pp. 110-111.
Devaney et al. Super-resolution Processing of Multi-Static Data Using Time Reversal and Music, 2000. {Online]: http://www.ece.neu.edu/faculty/devaney/ajd/preprints.htm, pp. 4,10.
Devaney et al., Time-reversal-based imaging and inverse scattering of multiply scattering point targets, 2005, the Journal of the Acoustical Society of America, vol. 118, No. 5, p. 3132.
Duric et al. "Development of Ultrasound Tomography for Breast Imaging: Technical Assessment," Medical Physics 32(5):1375-86.
Fichtner et al. "Full Seismic Waveform Tomography for upper-mantle structure in the Australasian region using Adjoint Methods," Geophys. J. Int. (2009) 179, pp. 1703-1725.
Huang et al., "A Rapid and Robust Numerical Algorithm for Sensitivity Encoding with Sparsity Constraints: Self-Feeding Sparse Sense," Magnetic Resonance in Medicine, 2010, 64:1078-1088.
Ikedo et al., Development of a fully automatic scheme for detection of masses in whole breast ultrasound images, 2007, Medical Physics, vol. 24, No. 11, pp. 4381.
Labyed et al., Ultrasound Time-Reversal Music Imaging with Diffraction and Attenuation Compensation, 2012, IEEE Transactions on Ultrasonics, Ferroelectrics, and Frequency Control, vol. 59, No. 10, p. 2188.
Lemoult et al., Time Reversal in Subwavelength-Scaled Resonant Media: Beating the Diffraction Limit, 2011, International Journal of Microwave Science and Technology, vol. 2011, Article ID 425710, p. 4.
Nguyen et al., The DORT solution acoustic inverse scattering problem of a small elastic scatterer, 2010, Ultrasonics, col. 50, Issue 8, pp. 831-832.
Sumi, C., "Spatially variant regularization for the Deconvolution of Ultrasonic Signals," Rev. of Prog. in Quantitative Nondestructive Evaluation, J Med Ultrasonics (2007) 34:125-131, Mar. 8, 2007.
Szabo et al. 2004, "Determining the pulse-echo electromechanical characteristic of a transducer using flat plates and point targets," the Journal of the Acoustical Society of America, vol. 116, No. 1, p. 91.

(56) References Cited

OTHER PUBLICATIONS

Tai, et al. "Image Denoising Using TV-Stokes Equation with an Orientation-Matching Minimization" Space and Variational Methods in Computer Vision, Lecture Notes in Computer Science, vol. 5567, 2009, pp. 1-12.
Tape et al., "Finite-Frequency Tomography Using Adjoint Methods-Methodology and Examples Using Membrane Surface Waves," Geophys. J. Int. (2007) 168, pp. 1105-1129.
Waag et al., A Ring Transducer System for Medical Ultrasound Research, 2006, IEEE Transactions on Ultrasonics, Ferroelectrics, and Frequency control, vol. 53, No. 10, p. 1709.
Yao et al., "A Fast Algorithm to Calculate Ultrasound Pressure Fields from Single-Element Transducers," 1989, IEEE Transactions on Ultrasonics, Ferroelectrics and Frequency Control, vol. 36, No. 4, pp. 446.
Korean Intellectual Property Office (KIPO), International Search Report and Written Opinion dated May 30, 2013, Counterpart PCT International Application No. PCT/US2013/024512, pp. 1-10, with claims searched, pp. 11-21.
Korean Intellectual Property Office (KIPO), International Search Report and Written Opinion dated May 30, 2013, PCT International Application No. PCT/US 2013/024550, pp. 1-11, with claims searched, pp. 12-21.

\* cited by examiner

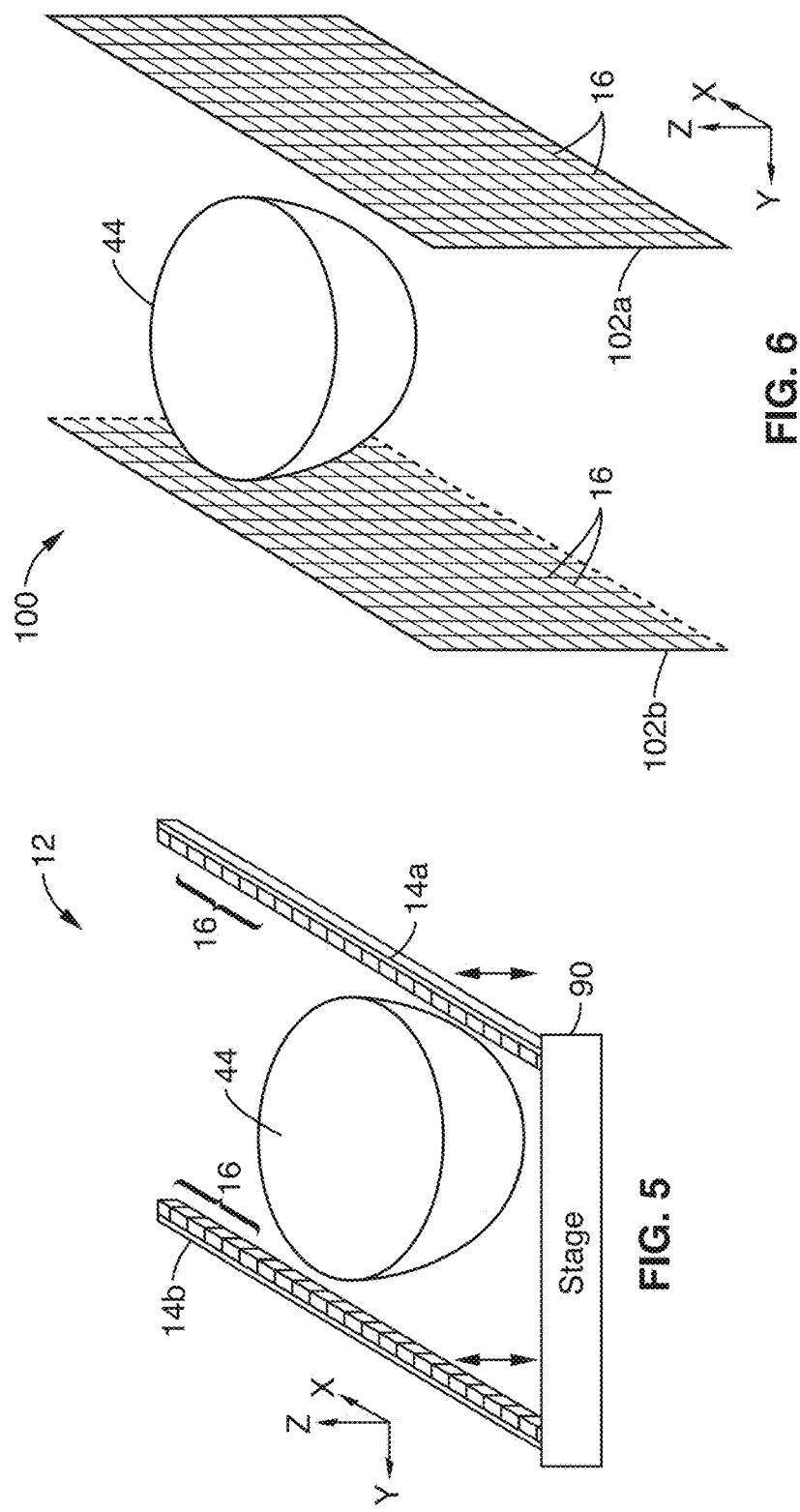

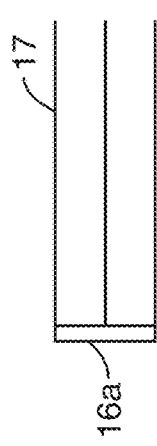
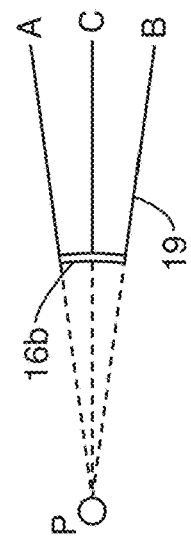
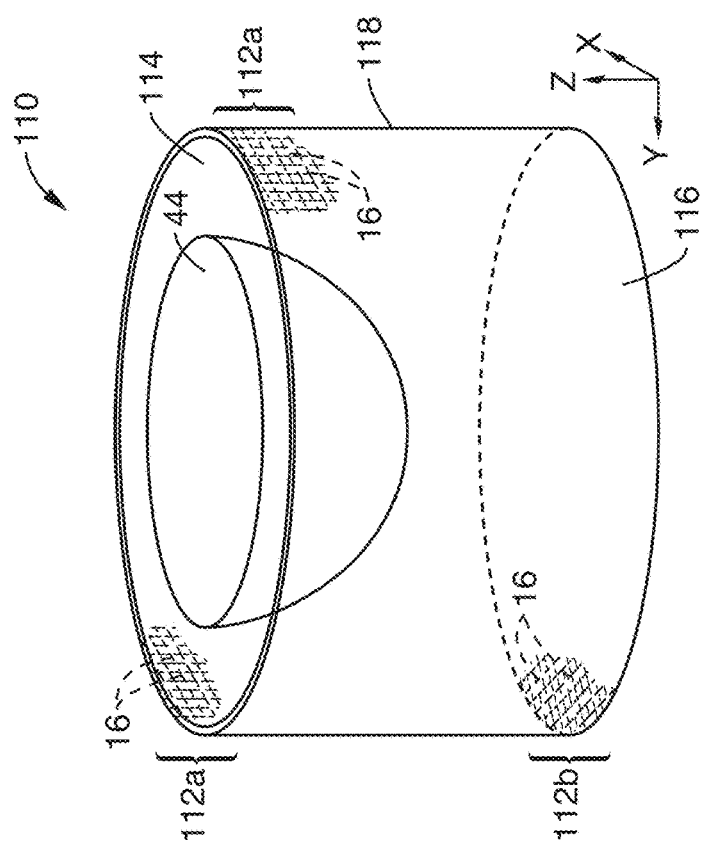
FIG. 8
FIG. 9
FIG. 7

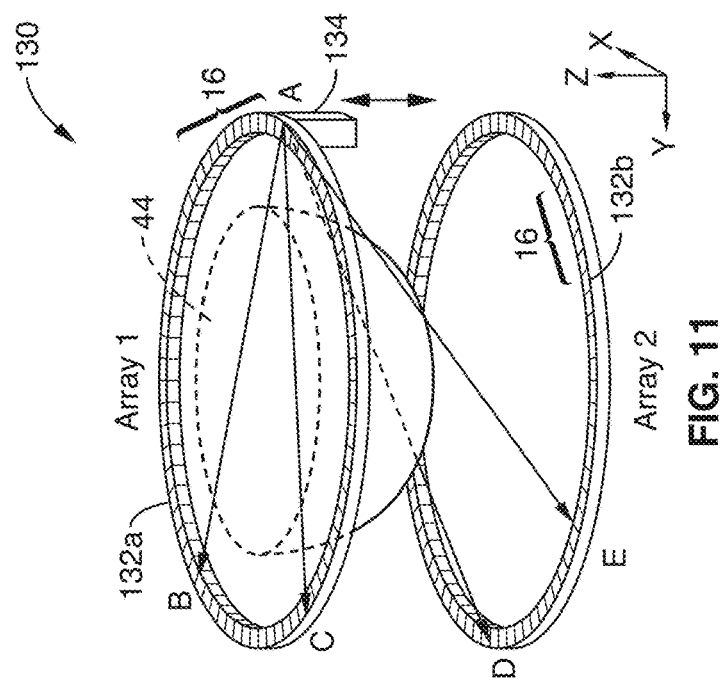
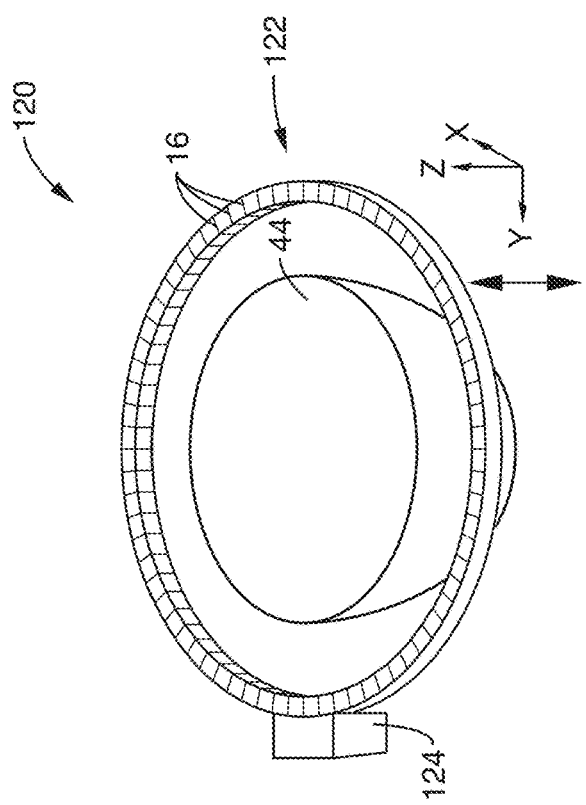
FIG. 11
FIG. 10

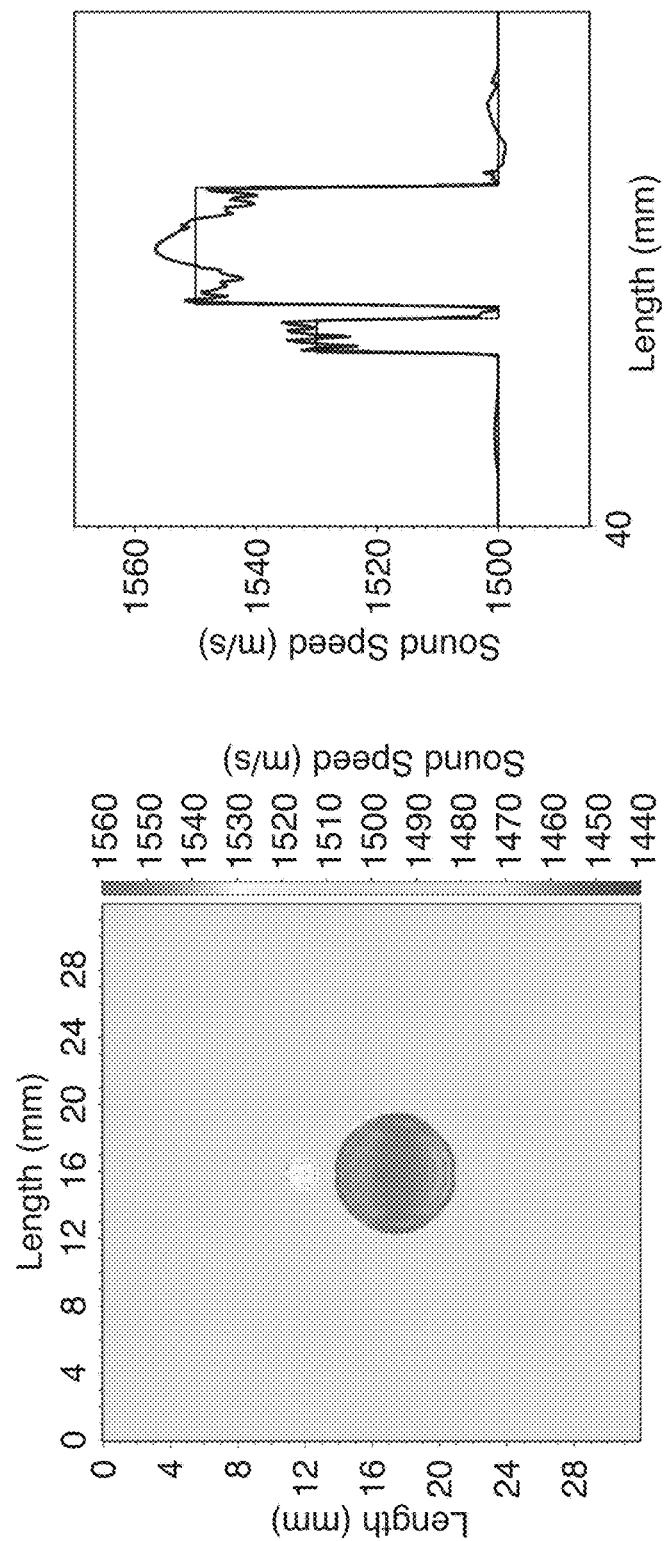

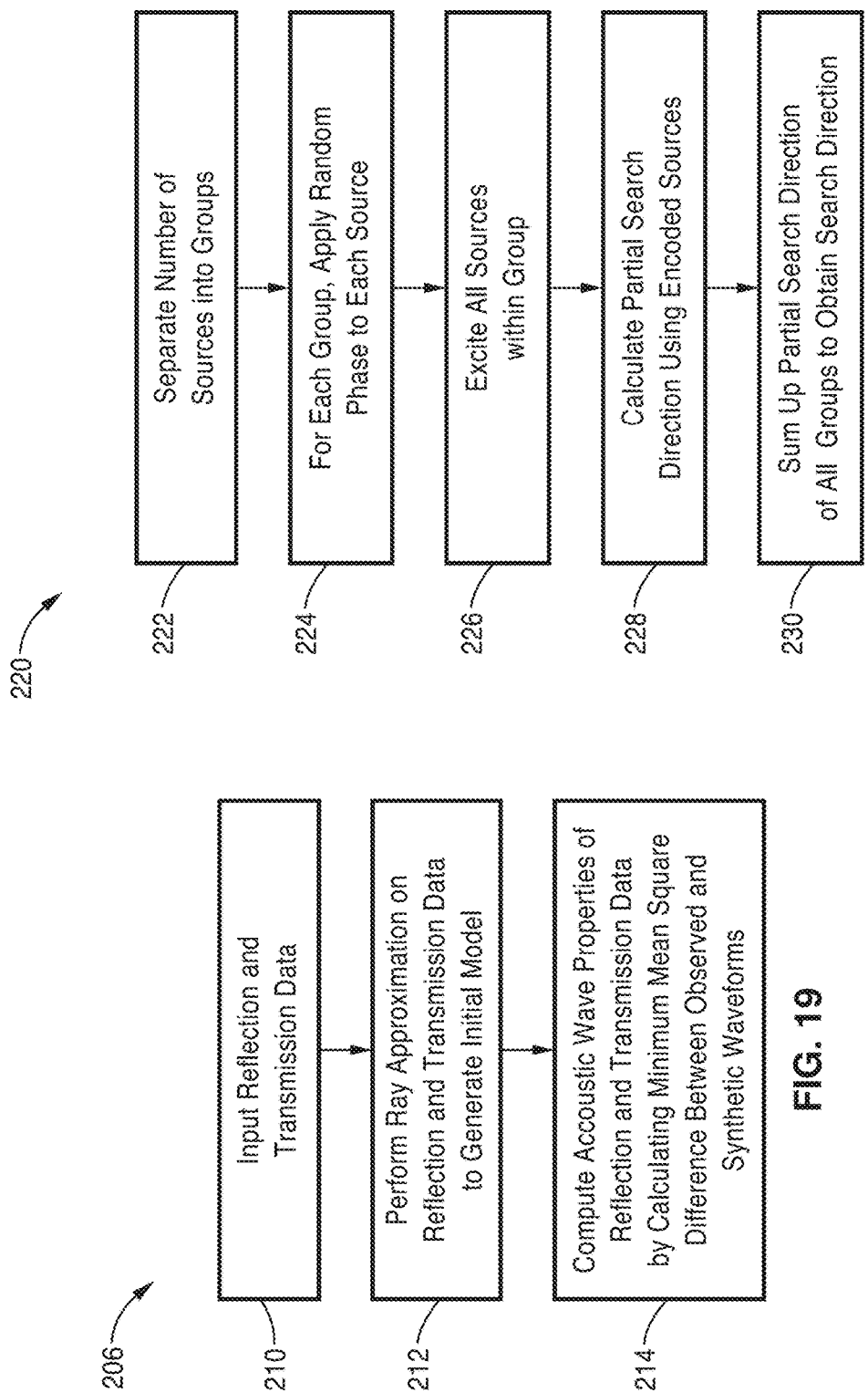

US 10,034,656 B2

SYSTEMS AND METHODS FOR INCREASING EFFICIENCY OF ULTRASOUND WAVEFORM TOMOGRAPHY

CROSS-REFERENCE TO RELATED APPLICATIONS

This application is a 35 U.S.C. § 111(a) continuation of PCT international application number PCT/US2013/024676 filed on Feb. 4, 2013, incorporated herein by reference in its entirety, which claims priority to, and the benefit of, U.S. provisional patent application Ser. No. 61/594,865, filed on Feb. 3, 2012, incorporated herein by reference in its entirety. Priority is claimed to each of the foregoing applications.

The above-referenced PCT international application was published as PCT International Publication No. WO 2013/116866 on Aug. 8, 2013, incorporated herein by reference in its entirety.

STATEMENT REGARDING FEDERALLY SPONSORED RESEARCH OR DEVELOPMENT

This invention was made with Government support under Grant No. MIPROLDATM0144 from the Breast Cancer Research Program of DoD-Congressionally Directed Medical Research Programs and Contract No. DE-AC52-06NA25396 awarded by the Department of Energy. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging, and more particularly to ultrasound imaging using a synthetic aperture ultrasound waveform tomography.

2. Description of Related Art

Breast cancer is the second-leading cause of cancer death among American women. The breast cancer mortality rate in the U.S. has been flat for many decades, and has decreased only about 20% since the 1990s. Early detection is the key to reducing breast cancer mortality. There is an urgent need to improve the efficacy of breast cancer screening. Ultrasound tomography is a promising, quantitative imaging modality for early detection and diagnosis of breast tumors.

Ultrasound waveform tomography is gaining popularity, but is computationally expensive, even for today's fastest computers. The computational cost increases linearly with the number of transmitting sources.

Waveform tomography accounts for all the wave propagation effects, and is more powerful than diffraction tomography. It is usually carried out with a numerical simulator and is capable of properly handling complex wave phenomena. However, ultrasound waveform tomography is computationally expensive for data acquired using a synthetic-aperture ultrasound tomography system, particularly for three-dimensional imaging. Ultrasound waveform tomography numerically calculates sound-wave propagation from every ultrasound transducer element. In a synthetic-aperture ultrasound tomography system, hundreds to thousands of transducer elements emit ultrasound, which requires an enormous amount of computational time and resources for ultrasound waveform tomography Ultrasound waveform tomography could become a high-resolution imaging approach for breast cancer detection and diagnosis. The main disadvantage of ultrasound waveform tomography is too computationally expensive to be feasible for clinical applications, particularly for large datasets acquired using a synthetic-aperture ultrasound tomography system that consists of hundreds to thousands of transducer elements.

BRIEF SUMMARY OF THE INVENTION

An aspect of the present invention is a source encoding method for ultrasound waveform tomography to greatly improve the computational efficiency. This method simultaneously simulates ultrasound waves emitted from multiple transducer elements during inversion. A random phase is applied to each source to distinguish the effect of different sources. The random phase helps eliminate the unwanted cross interference produced by different sources. The method significantly reduces the computational time of ultrasound waveform tomography to less than one tenth of that for the original ultrasound waveform tomography, and makes it feasible for ultrasound waveform tomography in future clinical applications.

Another aspect is a source encoding scheme for ultrasound waveform tomography using transmission and reflection data from synthetic-aperture ultrasound tomography systems. The method simultaneously simulates ultrasound propagation from tens to hundreds of transducer elements during inversion. The approach employs a random phase on each transducer element to remove the cross interference.

The system and method of the present invention uses ultrasound data acquired using a synthetic-aperture ultrasound system. The investigational synthetic-aperture ultrasound tomography system of the present invention allows acquisition of each tomographic slice of patient ultrasound data in real time. In the system, each element of the transducer array transmits ultrasound sequentially, and elements in the transducer array simultaneously record ultrasound signals scattered from the tissue after each element is fired. The features of the system and method of the present invention provide a real-time synthetic-aperture system that can be used for patient data acquisition.

In the synthetic-aperture ultrasound tomography system of the present invention, ultrasound from each element of a transducer array or a virtual source of multiple elements propagates to the entire imaging domain, and all elements in the transducer array receive ultrasound signals reflected/scattered from the imaging region and/or transmitted/scattered through the imaging region. Therefore, the acquired synthetic-aperture ultrasound data contain information of ultrasound reflected/scattered and transmitted from all possible directions from the imaging domain to the transducer array to generate a more accurate, 3-D, high resolution image, while minimizing computational costs of the system.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 5 illustrates a schematic view of a two parallel-bar ultrasound transducer array scanner.

FIG. 6 illustrates a schematic view of a scanner comprising two parallel planar arrays.

FIG. 7 shows a schematic view of a cylindrical array scanner having a cylindral 2-D array of transducers and a 2-D planner array at the bottom of the cylinder.

FIG. 8 shows a flat transducer configured to generate a collimated beam.

FIG. 9 shows an arcuate transducer configured to generate a diverging beam.

FIG. 10 shows a schematic view of a toroidal array scanner having a a circular array of transducers.

FIG. 11 shows a schematic view of a synthetic-aperture ultrasound breast tomography scanner that incorporates use of two circular transducer arrays.

FIG. 18A and FIG. 18B show imaging results (tomographic reconstruction in FIG. 18A, and vertical profile along the center of the tumors in FIG. 18B) obtained using both transmission and reflection data simultaneously in accordance with method of the present invention.

FIG. 19 illustrates a method using both transmission and reflection data for ultrasound waveform tomography.

FIG. 20 illustrates a flow diagram of a source encoding method for ultrasound waveform tomography in accordance with the present invention.

Figure 23A:
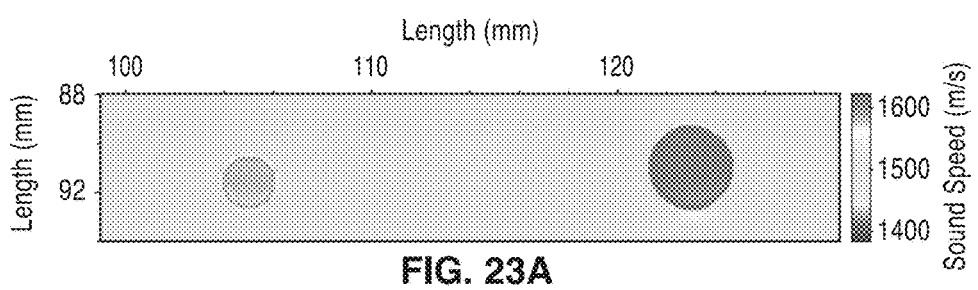
Figure 23B:
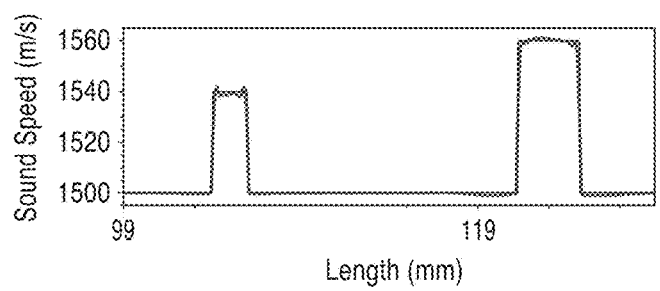
Figure 24A:
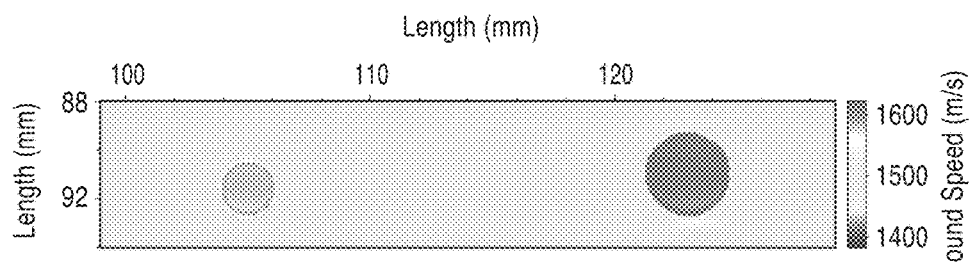
Figure 24B:
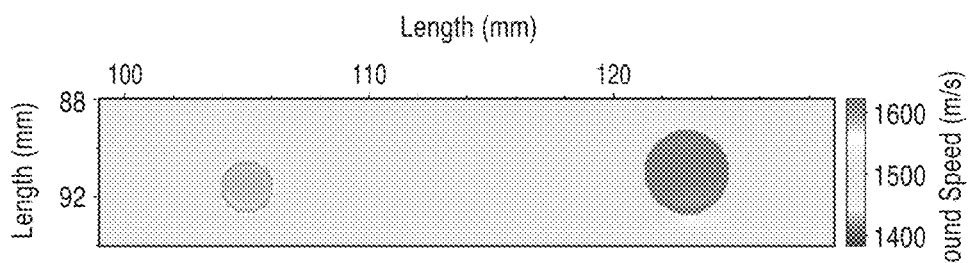
Figure 24C:
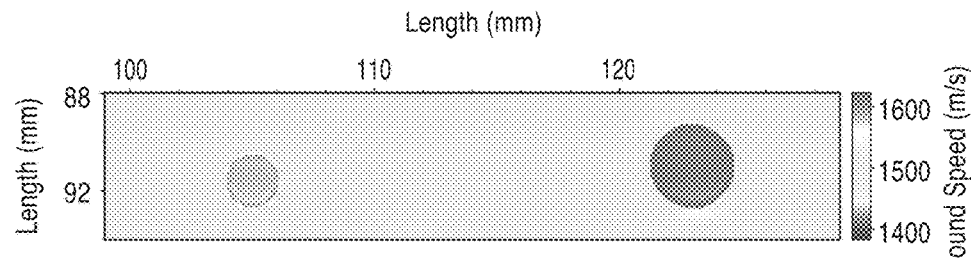
Figure 24D:
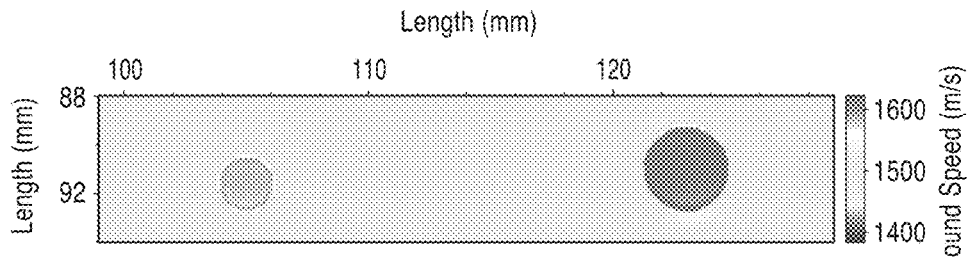
Figure 25A:
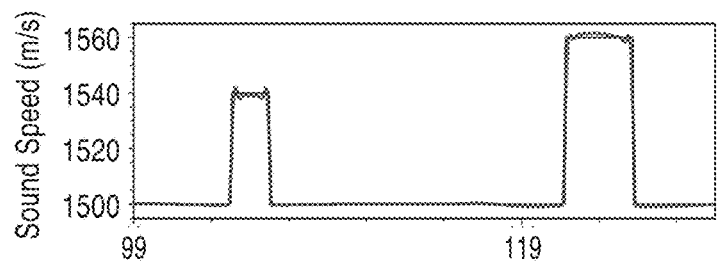
Figure 25B:
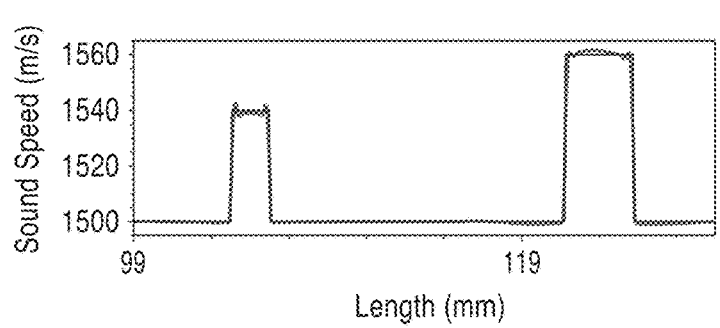
Figure 25C:
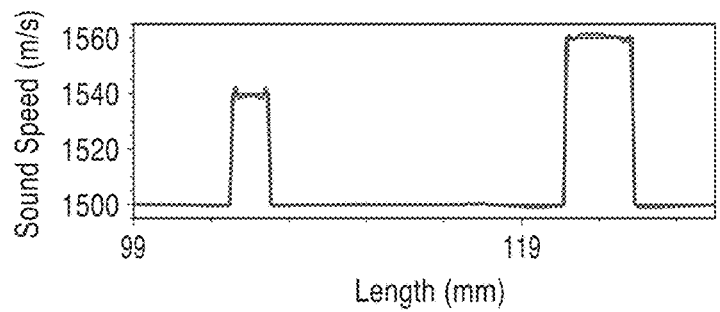
Figure 25D:
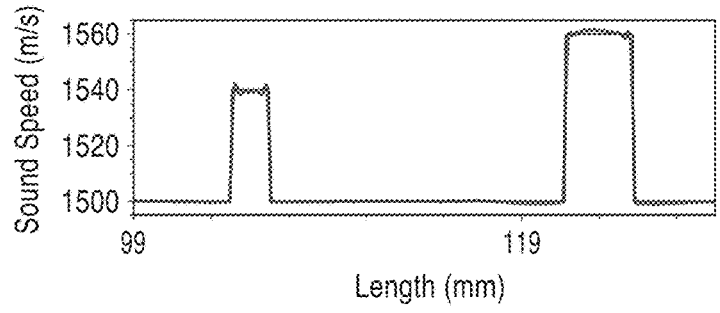
Figure 26A:
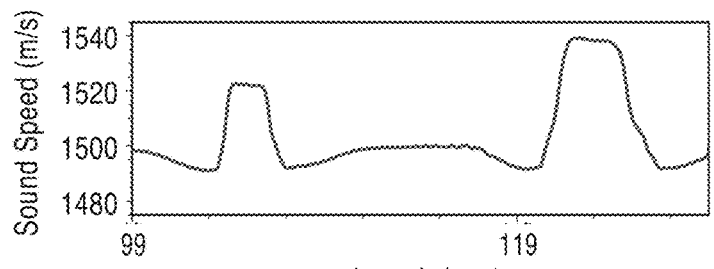
Figure 26B:
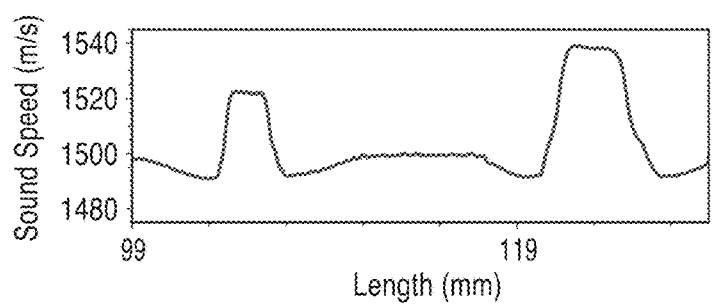
Figure 26C:
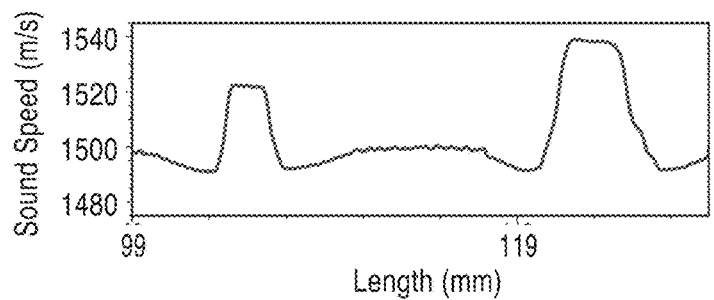
Figure 26D:
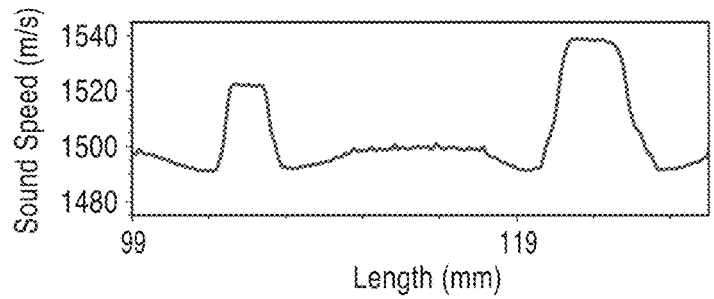

FIG. 23A and FIG. 23B show images of reconstruction results of ultrasound waveform tomography without source encoding obtained after 20 inversion iterations. FIG. 23A is a 2D image of the original ultrasound waveform tomography. FIG. 23B is a horizontal sound-speed profile of the tomography result at the vertical location of 91 mm.

FIG. 24A through FIG. 24D show images of ultrasound waveform tomography results obtained using source encoding after 20 iterations for 4, 8, 12 and 24 sources respectively.

FIG. 25A through FIG. 25D show images of horizontal sound-speed profiles of FIG. 24A through FIG. 24D at the vertical location of 91 mm for 4, 8, 12 and 24 sources respectively.

FIG. 26A through FIG. 26D show images of horizontal sound-speed profiles of the third-iteration result when using source encoding for 4, 8, 12 and 24 sources respectively. The vertical location of the profile is at 91 mm.

Figure 1:
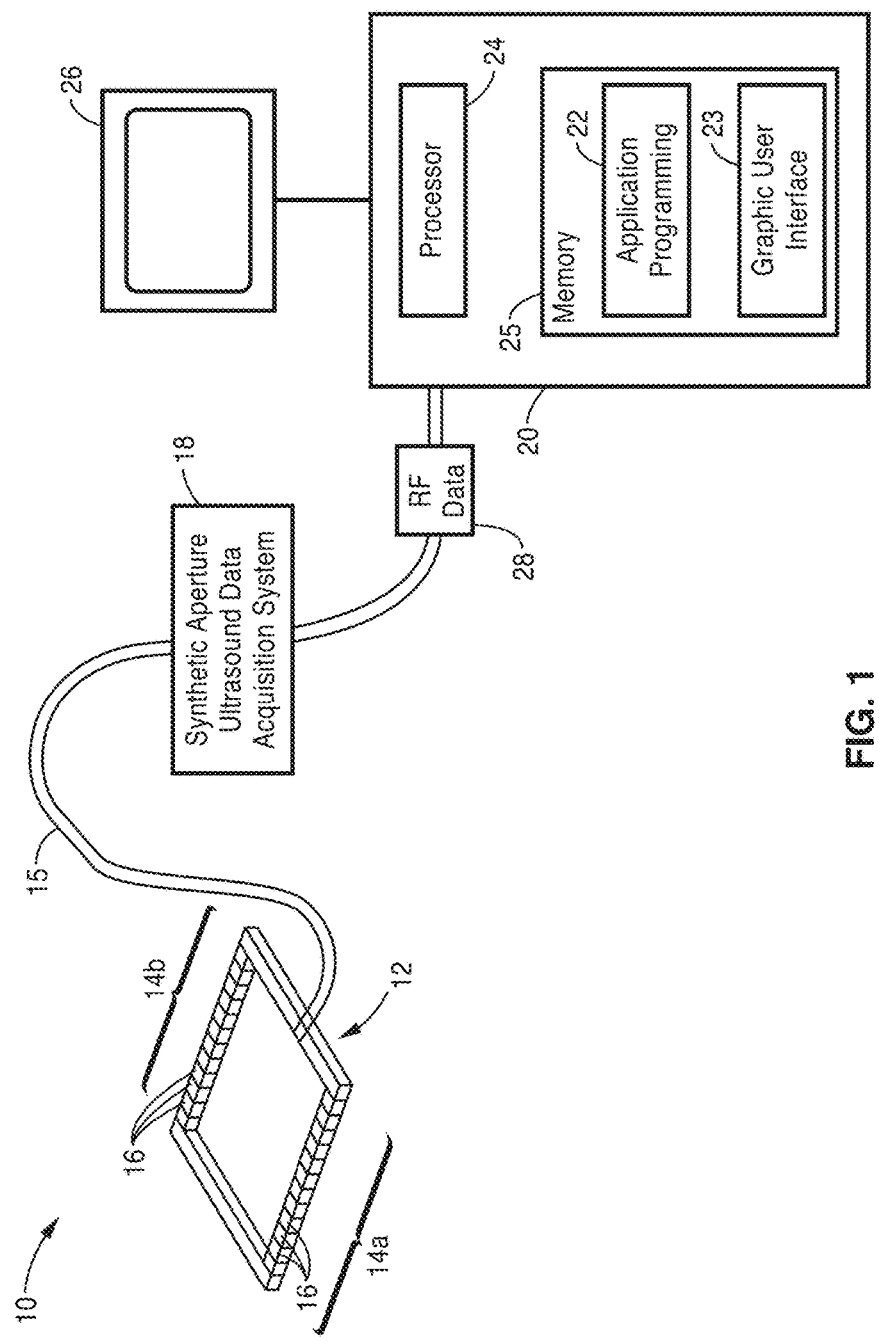
FIG. 1 is a schematic diagram of a synthetic-aperture ultrasound system in accordance with the present invention.
Figure 27:
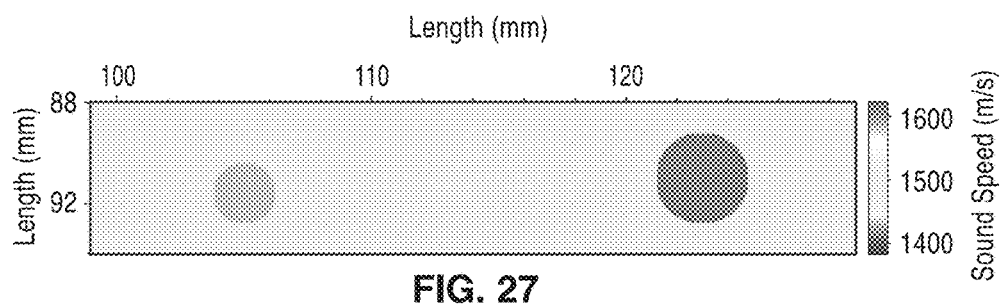

FIG. 27 shows an image of two small tumors in the numerical breast phantom scanned using the synthetic-aperture ultrasound tomography system similar to that shown in FIG. 1.

Figure 28A:
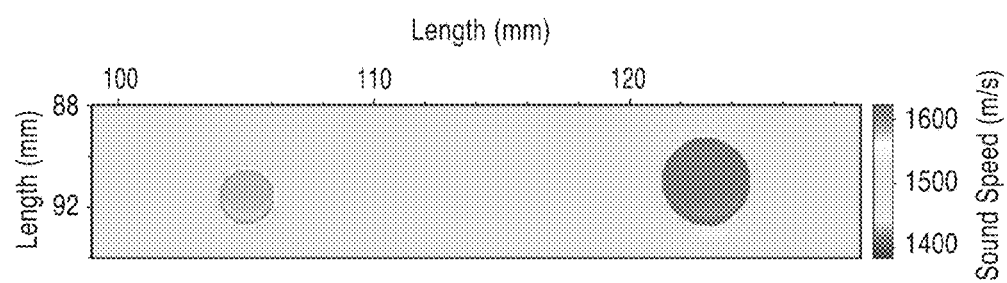
Figure 28B:
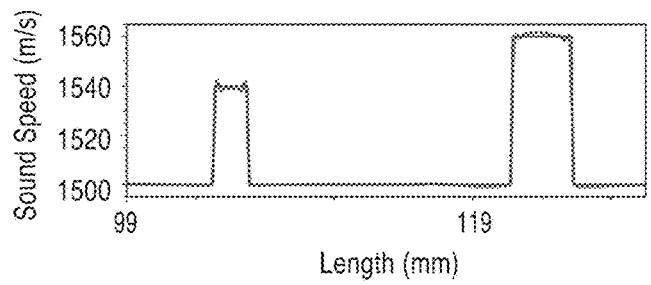

FIG. 28A and FIG. 28B show images of reconstruction results of ultrasound waveform tomography without data blending obtained after 20 inversion iterations. FIG. 28A is a 2D image of the original ultrasound waveform tomography. FIG. 28B is a horizontal sound-speed profile of the tomography result at the vertical location of 91 mm.

Figure 29A:
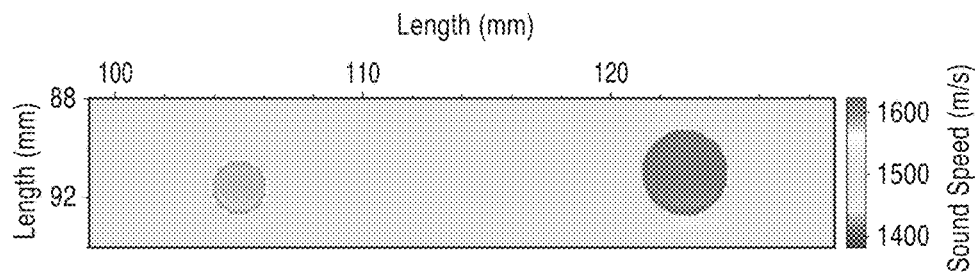
Figure 29B:
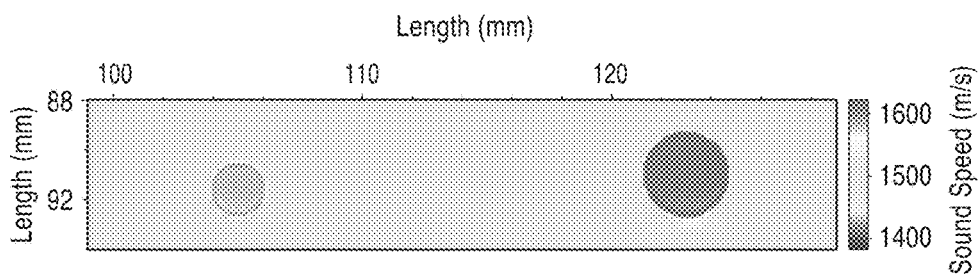
Figure 29C:
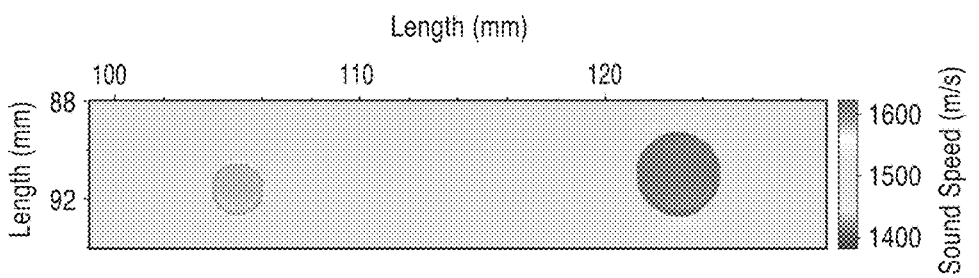

FIG. 29A through FIG. 29C show images of ultrasound waveform tomography results obtained using data blending after 20 iterations for 4, 8, and 24 sources respectively. The maximum delay time is one period.

Figure 30A:
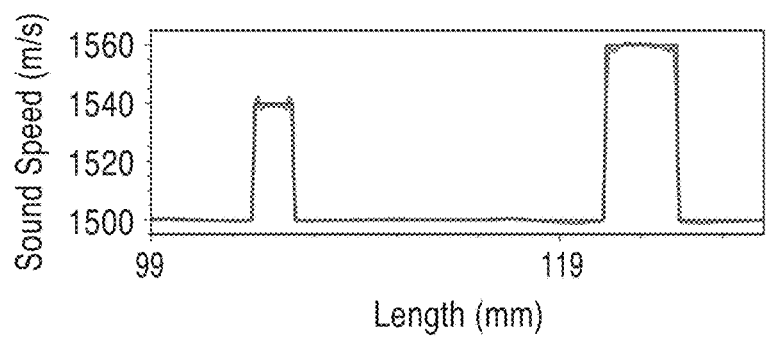
Figure 30B:
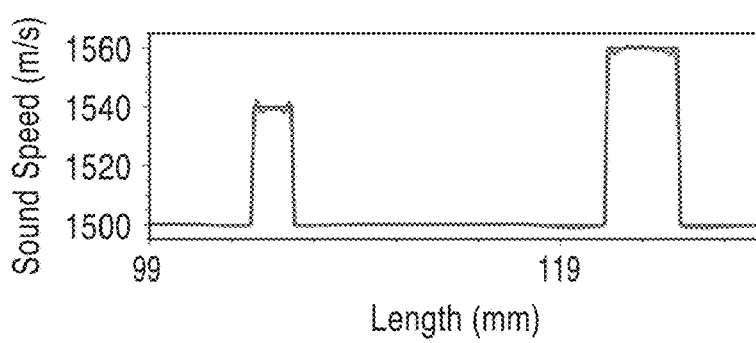
Figure 30C:
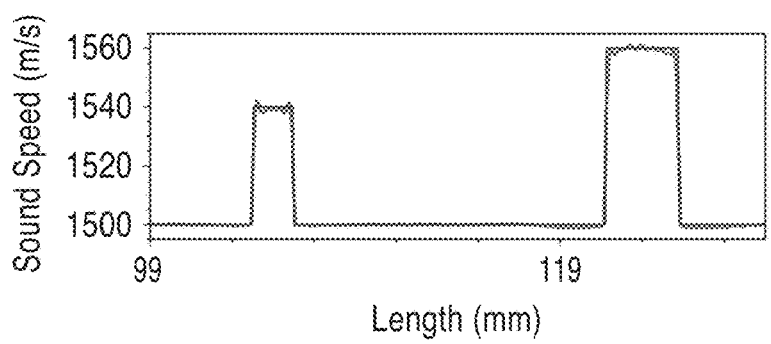

FIG. 30A through FIG. 30C show images of horizontal sound-speed profiles of FIG. 29A through FIG. 29C at the vertical location of 91 mm for 4, 8, and 24 sources respectively.

Figure 31A:
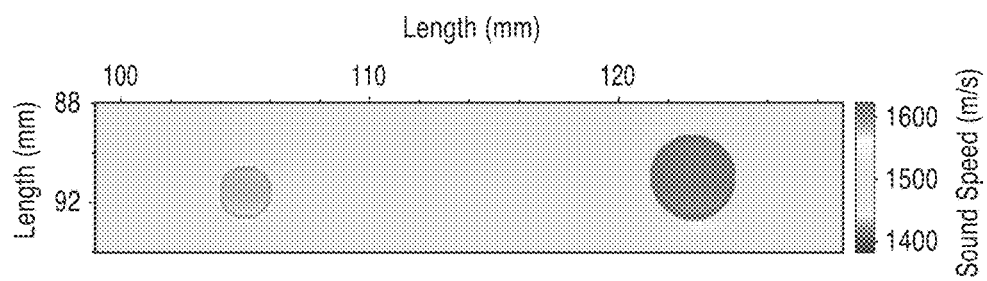
Figure 31B:
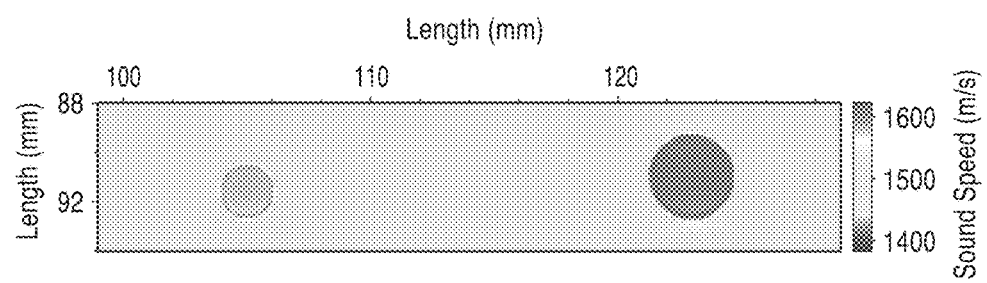
Figure 31C:
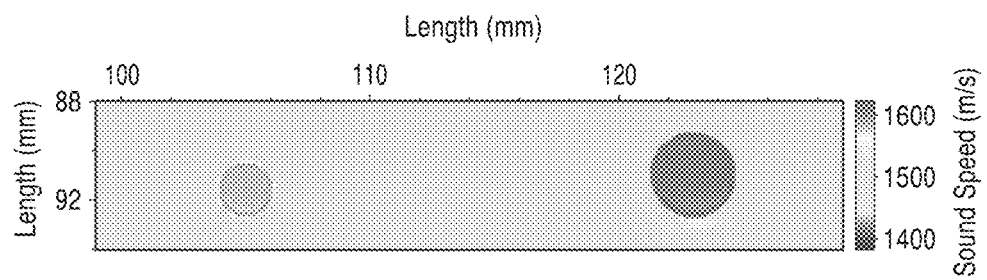

FIG. 31A through FIG. 31C show images of ultrasound waveform tomography results obtained using blended data after 20 iterations for 4, 8, and 24 sources respectively. The maximum delay time is one period.

Figure 32A:
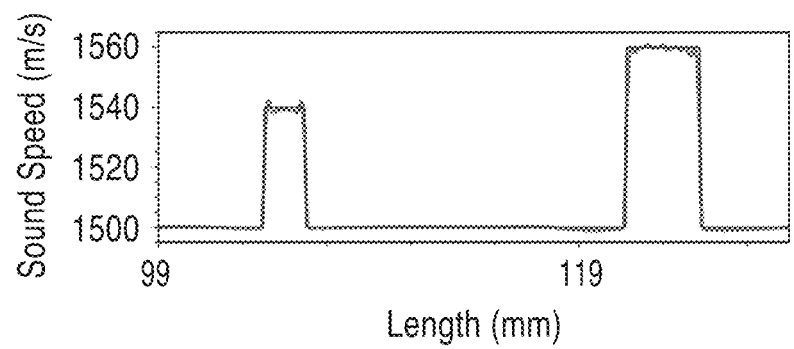
Figure 32B:
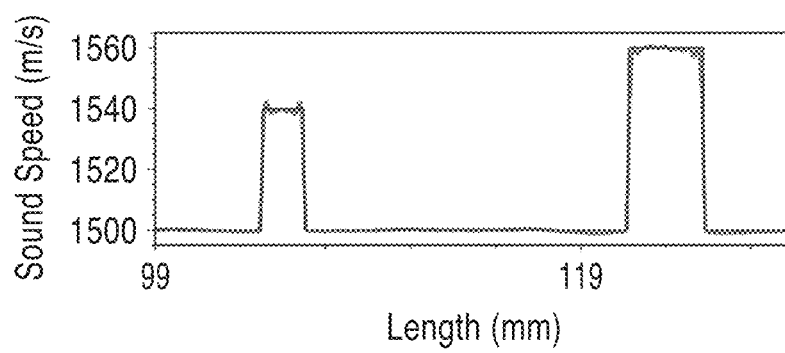
Figure 32C:
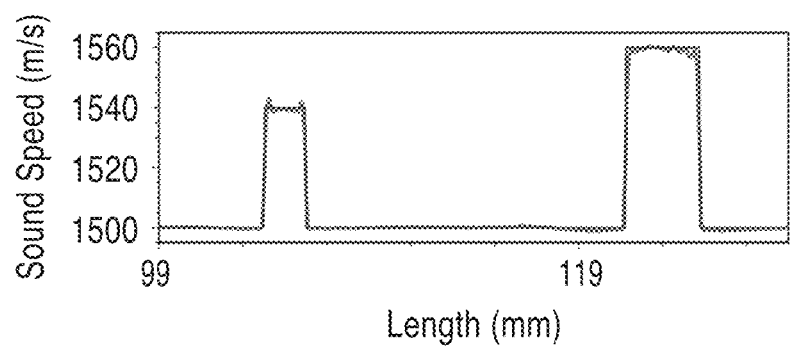

FIG. 32A through FIG. 32C show images of horizontal sound-speed profiles of FIG. 31A through FIG. 31C at the vertical location of 91 mm for 4, 8, and 24 sources respectively.

Figure 33A:
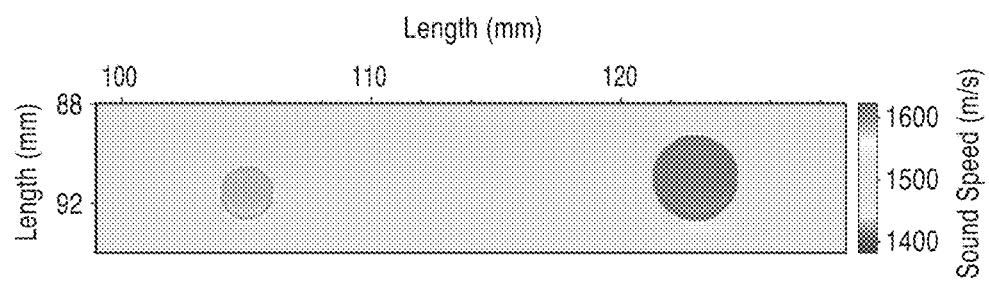
Figure 33B:
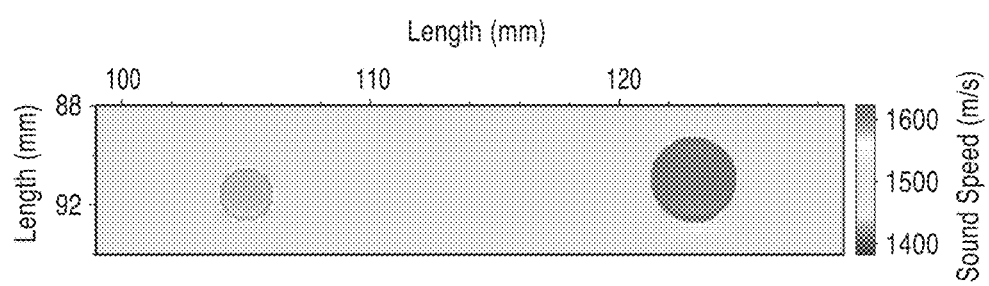
Figure 33C:
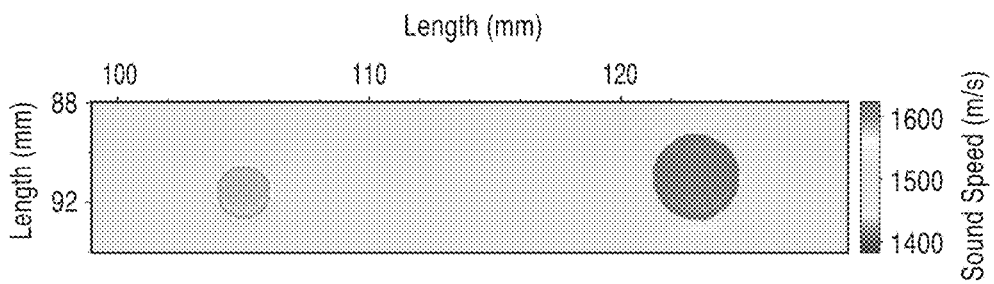

FIG. 33A through FIG. 33C: show images of ultrasound waveform tomography results obtained using blended data after 20 iterations for 4, 8, and 24 sources respectively. The maximum delay time is one period.

Figure 34A:
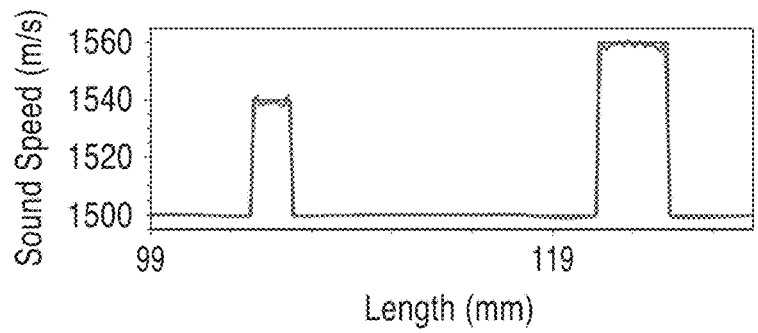
Figure 34B:
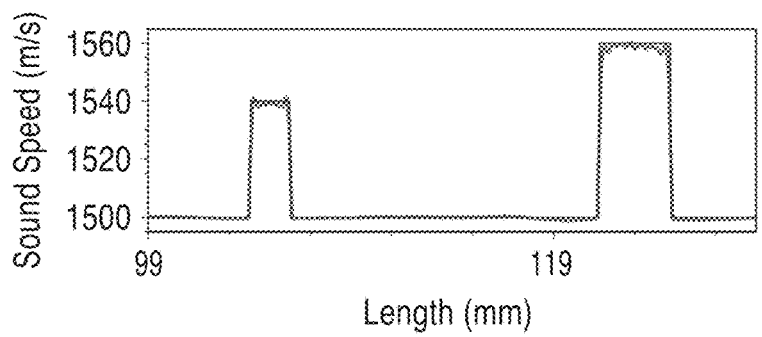
Figure 34C:
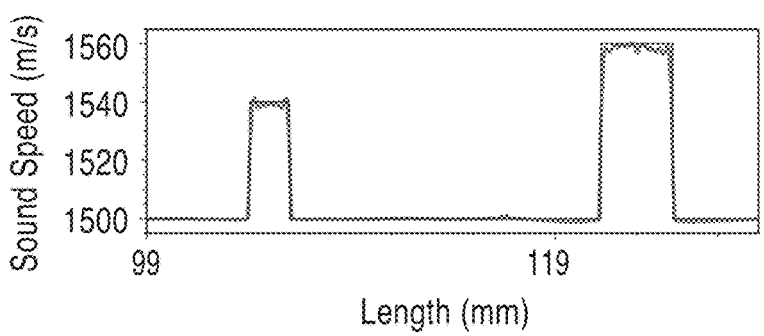

FIG. 34A through FIG. 34C show images of horizontal sound-speed profiles of FIG. 33A through FIG. 33C at the vertical location of 91 mm for 4, 8, and 24 sources respectively.

DETAILED DESCRIPTION OF THE INVENTION

The description below is directed to synthetic aperture ultrasound tomography systems for imaging a medium such as patient tissue, along with ultrasound waveform tomography methods for acquiring and processing data acquired from these systems, or other systems that may or may not be available in the art.

The synthetic-aperture breast ultrasound tomography system of the present invention uses synthetic-aperture ultrasound to obtain quantitative values of mechanical properties of breast tissues. In this system, each transducer element transmits ultrasound waves sequentially, and when an ultrasound transducer element transmits ultrasound waves propagating through the breast, all ultrasound transducer elements (at least within a portion of an array) simultaneously receive ultrasound reflection/transmission, or forward and backward scattering signals. The ultrasound reflection/transmission signals are used to obtain quantitative values of mechanical properties of tissue features (and in particular breast tumors), including the sound speed, density, and attenuation.

While the systems and methods described below are particularly directed and illustrated for imaging of breast tissues, it is appreciated that the systems and methods may also be employed for waveform tomography on other tissues or scanning mediums.

I. Synthetic Aperture Ultrasound Tomography System

FIG. 1 is a schematic diagram of a synthetic-aperture ultrasound system 10 in accordance with the present invention. The system 10 includes a scanner 12 comprising a plurality of individual transducer elements 16 disposed within one or more arrays (e.g. the opposing parallel arrays 14a and 14b shown in FIG. 1). The scanner 12 is coupled to a server or like computing apparatus 20 (e.g. with a cable 15 or other connection means such as, but not limited to, a wireless connections means) and synthetic aperture ultrasound data acquisition system 18 that outputs RF data 28 corresponding to readings acquired by the scanner 12.

The computer 20 comprises a processor 24 configured to operate one or more application programs 22 located within memory 25, wherein the application programs 22 may contain one or more algorithms or methods of the present invention for imaging a tissue medium for display via a graphical user interface 23 on monitor 26, or other means. For example, the application programming 22 may comprise the programming configured for operating the sequential excitation method 50 shown in FIG. 4 or ultrasound waveform tomography imaging method 200 shown in FIG. 14. The computer 20 controls ultrasound tomography data acquisition, and the process is completed automatically. The whole-breast scanning time with approximately 100 slides takes approximately 2 minutes.

Figure 2:
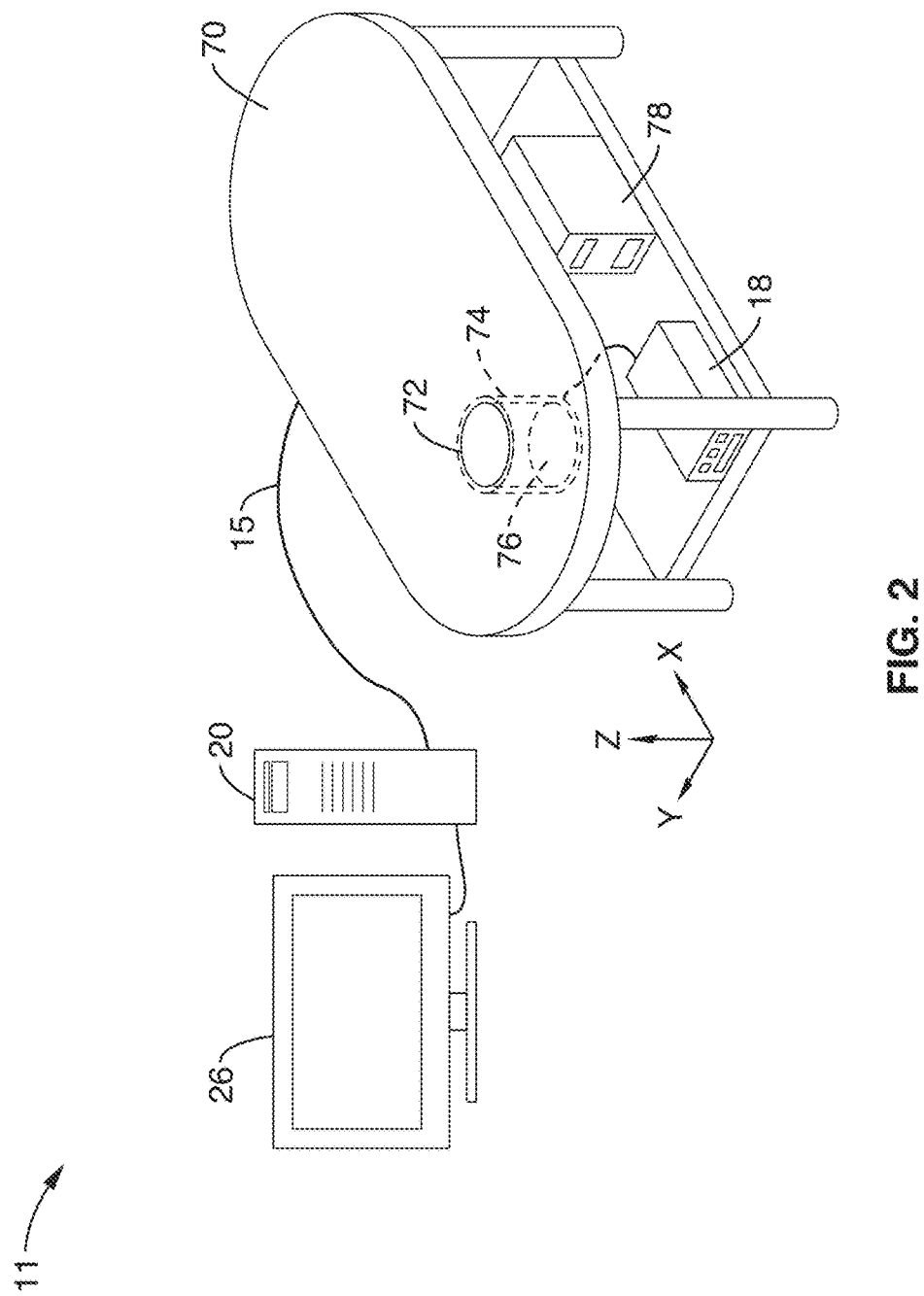
FIG. 2 is a schematic diagram of a synthetic-aperture ultrasound tomography system for scanning breast tissue in accordance with the present invention

FIG. 2 is a schematic view of a breast ultrasound tomography system 11 in accordance with the present invention. System 11 includes a table 70 having a water tank 76 with an open aperture at the top of the table 70 for insertion of the patient's breast tissue (which ideally hangs pendant within water tank 76 during imaging). Tank 76 includes one or more synthetic-aperture ultrasound transducer arrays 74 located within one or more surfaces of the tank. The transducer array(s) 74 are immersed within the water tank 76 configured for receiving the patients breast 44 through aperture 72, and scanning the breast 44 while the patient is lying down on the table 70 in the prone position. As described in further detail below, transducer array(s) 74 may comprise a number of different configurations, with the water tank housing 76 shaped accordingly to house the array(s) 74. The water tank housing 76 material preferably comprises a light, non-conductive material that conforms to the shape of the array(s) 74 (e.g. rectangular for 2-parallel bar array scanner 12 of FIG. 1, or cylindrical for the scanners 110, 120 and 130 shown in FIG. 7, FIG. 10 and FIG. 11, respectively).

Positioning of the active areas of all array(s) 74 relative to the water tank housing 76 is preferably aligned such that the ultrasound energy for the transducer elements 16 (FIG. 1) is focused onto the same plane perpendicular to the housing (for parallel bar scanner 12 (FIG. 5) or planar 100 (FIG. 6) arrays). The arrays (e.g. arrays 14a and 14b, FIG. 1) are preferably electrically isolated and grounded.

The system 11 includes a data acquisition system 18 that may be coupled to a computer system or electronics 78 that control scanning. The data acquisition system 18 may also be coupled to a computer 20 for running application programming 22 (FIG. 1) to perform tomography reconstructions.

During the ultrasound data acquisition in the synthetic-aperture ultrasound tomography system 10, the raw ultrasound data 28 (radio-frequency data) may be first stored within computer memory 25 (FIG. 1) (which may comprise solid state drives or other storage means available in the art), allowing real-time patient data acquisition for clinical applications.

Figure 3:
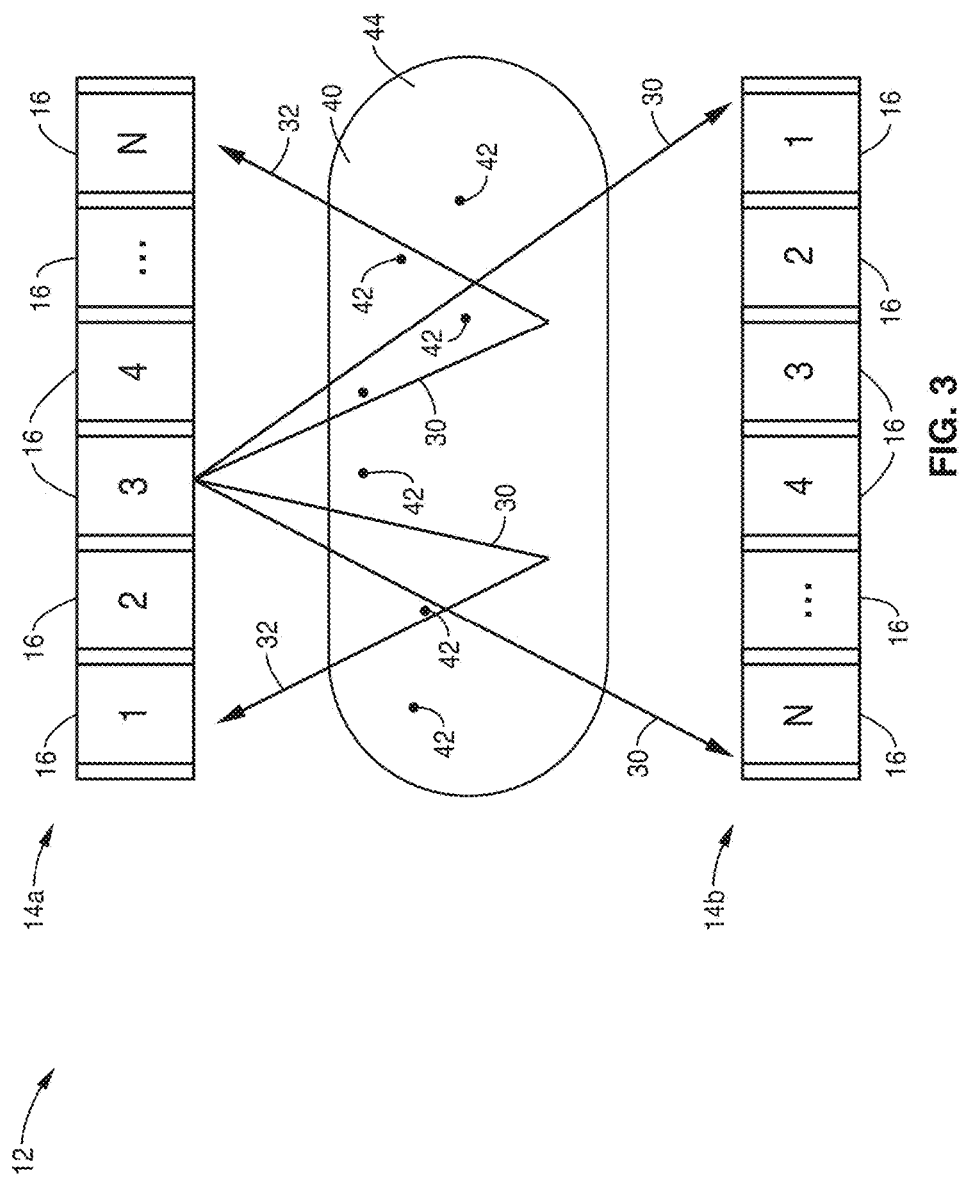
FIG. 3 is a schematic diagram of the scanner of the ultrasound tomography system of FIG. 1 interrogating a region of tissue.

FIG. 3 is a schematic diagram of the two parallel bar arrays 14a and 14b of scanner 12 of FIG. 1 shown interrogating a region of tissue 44 (e.g. breast tissue for mammography) in accordance with a preferred method of the present invention. The ultrasound imaging system 10 focuses an array 14a and 14b of N transducers 16 acting in a transmit-receive mode. Each element of the array 14a 14b is excited sequentially (e.g. transducer 3 of array 14a is shown in excitation mode) to generate an ultrasound field or signal 30 through the tissue surface 40 and into tissue medium 44 having a plurality of point scatterers 42. The backscattered signals 32 are measured in parallel by all N elements 16. In addition, opposing array 14b transducers are positioned facing array 14a such that one or more elements of the array 14b receive direct transmission signals 30 simultaneously with reception of backscatter or reflection signals 32 being received by array 14a.

Figure 4:
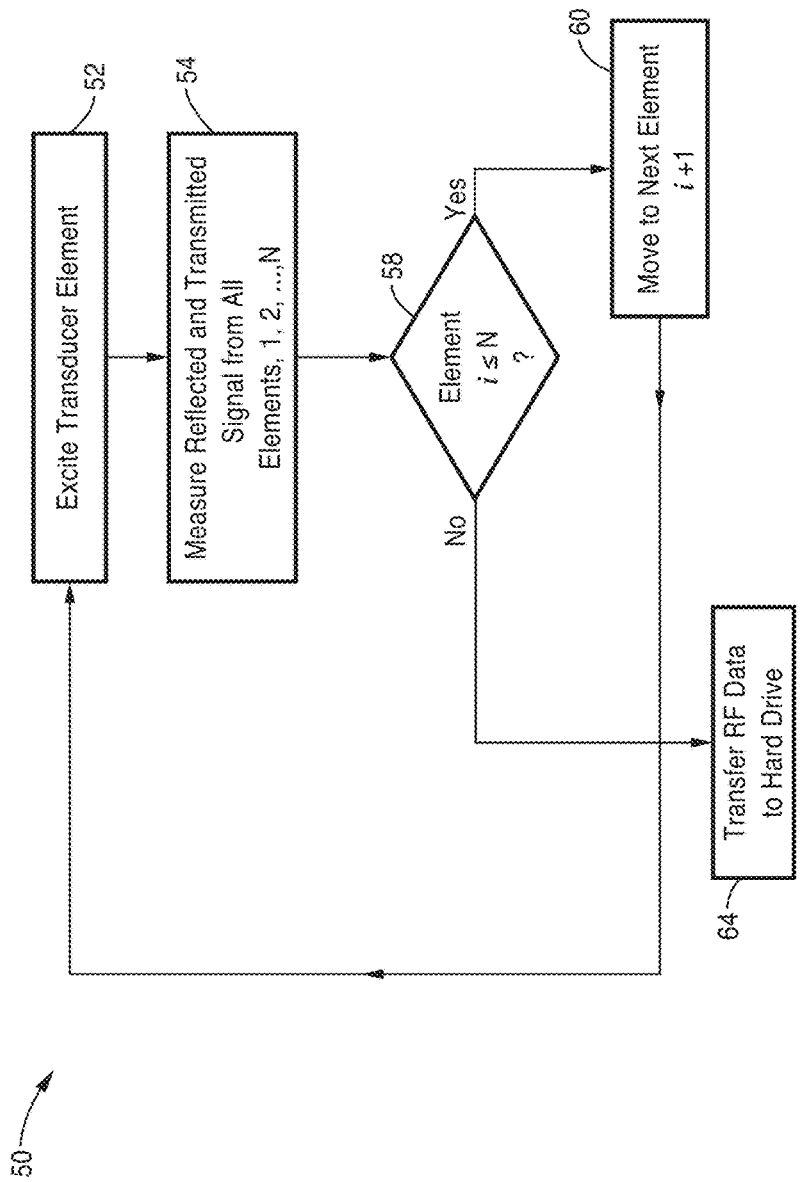
FIG. 4 shows flow diagram of a method for sequentially exciting a region of tissue and acquiring reflection and transmission data in accordance with the present invention.

FIG. 4 shows flow diagram of a method 50 for sequentially exciting a region of tissue 44 in accordance with the present invention. At step 52, a first element (e.g. element 1 or i) of array 14a 14b of N ultrasound transducer elements 16 is excited for interrogating an inhomogeneous medium 44. At step 54, the backscattered/reflected signals 32 are received/measured by all elements 16 (of at least 14a), while transmission signals 30 are received/measured by one or more elements 16 of array 14b. At step 58, the method evaluates whether all the elements 16 in the arrays 14a and 14b have been excited (and imaged). If the last element in the arrays 14a, 14b has not been reached, the method moves to the next element 16 in the array (14a or 14b) at step 60, and repeats the process sequentially until the $N^{th}$ element is reached. At this point, the individual reflection/transmission data are RF data, and the process 50 transfers the RF data to memory or solid state drives 25 at step 64.

In the phased transducer arrays for synthetic-aperture breast ultrasound tomography, a plurality of transducer elements 16 are fired with different delayed times to simulate ultrasound waves emerging from a virtual point source. The systems and methods of the present invention preferably use the virtual point sources of the synthetic-aperture breast ultrasound tomography system to improve signal-to-noise ratios of breast ultrasound data.

The various scanning arrays invention, described below with reference to FIG. 5 through FIG. 7 and FIG. 10 through FIG. 13, are shown to illustrate that the systems 10, 11 and methods 50, 200 may be achieved in various configurations. Yet, the scanning arrays of FIG. 5 through FIG. 7 and FIG. 10 through FIG. 13 all share at least one common characteristic in that at a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation. The following are specific examples of arrays that may be used in the systems 10, 11 and methods 50, 200 of the present invention. However, other configurations are contemplated. In each of these configurations, the scanner 74 is shown without table 70 or housing 76 for clarity.

A. Dual Parallel-Bar Array Scanner

FIG. 5 illustrates a two parallel-bar ultrasound transducer array scanner 12, which is illustrated in reference to implementation within system 10 in FIG. 1, and schematically in operation as a synthetic-aperture scanner in FIG. 3.

As shown in FIG. 5, the two arrays 14a and 14b are shown in opposing orientation (e.g facing eachother and matching in location along x-axis in FIG. 5), and positioned in the x-y plane (preferably parallel to table 70 in FIG. 2, such that they are spaced-apart across the scanning region 44. Each of the 14a and 14b comprises a plurality of N transducers 16 (e.g. count of 128) linearly aligned in series (shown in along the x-axis for reference) as parallel-phased arrays firing toward each other in operation (see FIG. 3).

A robotic stage 90 is provided so that the arrays can move in unison vertically along the z-axis to scan the tissue 44. The transducer arrays 14a and 14b are configured to scan the breast 44 from the chest wall to the nipple region, slice by slice. To image the axillary region (region of breast closest to the armpit of the patient, not shown), the two transducer arrays 14a and 14b can be steered toward the axillary region, with one of the transducer arrays placed near the axillary region. The axillary region, or basin, is important to oncologic surgeons, as it represents the principal lymphatic drainage region of the breast. Lymphatic metastasis from a malignant breast lesion will most often occur in this region.

Arrays 14a and 14b may also be translated (either in concert, or with respect to each other) in the x and y axes to closely conform to varying patient anatomy.

Referring to FIG. 8 and FIG. 9, the transducer 16 may either be flat or circular, and the surface of the transducer element 16 may either be flat, as in transducer 16a in FIG. 8, or arcuate in shape, as shown in transducer 16b of FIG. 9. The flat transducer 16a of FIG. 8 generates a collimated beam 17, whereas the curvilinear transducer 16b of FIG. 9 has a focal point P that is behind the emitting surface to generate a diverging beam 19 (defocused or lens configuration preferably in the y-z plane) across a field of view from A to B (centered on C). The curvilinear transducer 16b of FIG. 9 helps get a 3-D volume while scanning, and is particularly useful with line arrays such as those in FIG. 5, FIG. 10, FIG. 11, and FIG. 13.

In one embodiment, exemplary dimensions for the arrays 14a and 14b and transducers 16 are as follows: a length inside the water tank along X-axis (the horizontal direction) of 16 inches, with 19.2 inches along Y-axis (the horizontal direction) and 16 inches in height along Z-axis (the vertical direction). The distances from the ends of the ultrasound phased transducer arrays 14a and 14b to the inside walls of the water tank along X-axis are approximately 3.8425 inches. In one embodiment, the horizontal distance between the front surfaces of the two parallel phased ultrasound transducer arrays can be adjusted from 12 cm to 25 cm, with a 1 cm increment utilizing 14 different sets of spacer blocks. The accuracy and precision of the horizontal position is ideally 5 microns or better. The vertical travel (Z axis) of the two parallel ultrasound phased transducer arrays 14a and 14b is 10 inches from the top surface of the water level. The vertical travel step interval can be adjusted to any value, such as 0.25 mm, 0.5 mm, 1 mm, and 2 mm.

In one embodiment, array 14a, 14b parameters are as follows: center frequency of 1.5 MHz, bandwidth of ~80% bandwidth (−6 dB) (measured for two-way sound propagation energy), the open angle of ultrasound waves emitting from a single element at ~80°, with uniform transducer elements 16 (<1 dB variation, and uniform bandwidth for one-way sound propagation energy).

In one embodiment, the arrays 14a, 14b comprise 1.5 MHz arrays with 384 elements each, equally spaced along the array. In one example, the dimensions/characteristics of the transducer elements are as follows: elevation aperture: 15 mm, element width: 0.4 mm for 1.5 MHz arrays, elevation focus: 10 cm away from the transducer element, with all transducers configured to be aligned along the array and perpendicular to the elevation plane.

It is appreaciated that the above dimensions and configuration details are for reference purposes only, and such characteristics may be varied accordingly.

The advantage of the configuration of scanner 12, over, e.g. the planar arrays of FIG. 6, is that the system 10 is using a fewer number of transducer elements.

B. Dual Parallel Planar Array Scanner

FIG. 6 illustrates a scanner 100 comprising two parallel planar arrays 102a and 102b aligned opposing each other across the scanning medium 44. Arrays 102a and 102b each comprise matching grids of 2-D arrays of transducers 16 (e.g. transducers 16 share the same locations in their respective x-z planes shown in FIG. 6). With the planar arrays the scanner 100 generally does not need to be translated in the z (vertical) direction.

There are generally two limitations for the synthetic-aperture breast ultrasound tomography with the cylindrical or circular transducer arrays: (a) it is difficult to image the axillary region of the tissue 44; and (b) one size of the cylindrical or circular transducer array will either be undersized or oversized for most sizes of the breast.

Synthetic-aperture breast ultrasound tomography with two parallel planar ultrasound transducer arrays 102a and 102b can overcome these two limitations. As shown in FIG. 6, one planar/2D transducer array 102b can be placed close to the axillary region of the tissue 44. In addition, the distance between the two planar ultrasound transducer arrays 102a and 102b can be adjusted with respect to each other (either manually or with robotic stage 90 as shown in FIG. 5) to fit different sizes of the breast. The ultrasound transducer elements 16 can be in circular or rectangular shape, and the surface of the transducer element can be either flat or arc-shaped, as shown in FIG. 8 and FIG. 9.

C. Cylindrical Array Scanner

FIG. 7 shows a cylindrical array scanner 110 having a cylindrical 2-D array 112a of transducers 16 in the inside surface of the cylinder wall 118 of the ultrasound transducer array. A planar array of elements 112b may also be positioned on the bottom surface 116 of the cylinder, which would primarily capture backscattered signals.

With the singular cylindrical array scanner 110, a first half of the semi-cylinder elements 16 will be opposed to or facing the second half of the semi-cylinder elements 16, and thus be positioned to receive direct transmission signals 30

(see FIG. 3) at least at varying degrees of angles of incidence. Thus depending on the amount of defocusing within each transducer, a plurality, or all, of the non-emitting transducers 16 will be able to receive a direct transmission signal 30 (FIG. 3) (at varying degrees) from the emitting transducer 16, leading to a full 3D ultrasound tomography image of the breast.

The top end 114 of the cylinder is open, such that the breast tissue 44 is immersed into the cylindrical array scanner 110 with 2D ultrasound transducer elements 16 surrounding the tissue 44. As with previous embodiments, the ultrasound transducer elements 16 can be in circular or rectangular shape, and the surface of the transducer element can be either flat or arc-shaped, as shown in FIG. 8 and FIG. 9.

D. Torroidal (Circular) Array Scanner

FIG. 10 shows a toroidal array scanner 120 having a a circular array 122 of transducers 16 aligned in a ring that is configured to encircle the breast 44. A robotic stage 124 may be provided to allow for translation of the array 122 to and scan the breast 44 from the chest wall to the nipple region, slice by slice.

With the singular toroidal array scanner 120, a first half of the semi-circle elements 16 will be opposed to or facing the second half of the semi-circle elements 16, and thus be positioned to receive direct transmission signals 30 (see FIG. 3) at least at varying degrees of angles of incidence. Thus, depending on the amount of defocusing within each transducer, a plurality, or all, of the non-emitting transducers 16 will be able to receive a direct transmission signal 30 (at varying degrees) from the emitting transducer 16.

The circular array 122 preferably comprises defocused lens-transducer elements 16b as shown in FIG. 9, enabling 3-D breast ultrasound tomography. One advantage of the toroidal configuration 120 is using a fewer number of transducer elements compared to the cylindrical transducer array 110.

E. Dual Toroidal (Circular) Array Scanner

FIG. 11. shows another synthetic-aperture ultrasound breast tomography scanner 130 that incorporates use of two circular transducer arrays (upper circular array 132a and lower circular array 132b).

Image resolution depends, at least in part, on ultrasound illumination of the target medium 44. To increase the ultrasound out-of-plane illumination angle, an acoustic diverging lens 16b, as shown in FIG. 9, may be used to widen the elevation beam to the desired level (e.g. between points B and C in the upper circular array 132a and D and E in the lower circular array 132b (conically diverging beam)). Thus, the defocused ultrasound transducer elements 16b transmit ultrasound waves propagating not only to the transducer elements within the same circular array, e.g. between B and C in the upper ring 132a, but also to the other circular transducer array, e.g. between D and E in the lower ring 132b. The upper transducer array 132a may be configured to scan the breast 44 from the chest wall position to the nipple region. At each position, the lower transducer array 132b may move to different vertical position in the z-axis to acquire ultrasound data. This configuration leads to improved vertical resolution of breast ultrasound tomography images compared that obtained using one circular transducer array as shown in FIG. 10.

In practice, the two circular ultrasound transducer arrays 132a and 132b are immersed into the water tank 76 and both encircle the breast 44. One or both arrays 132a and 132b may be configured to translate vertically via a motorized stage 134. For example, during an ultrasound scan, the upper cirular array 132a can be positioned against the chest wall, while the lower cirular array 132b moves upward from below the nipple region, or vice versa.

As with previous embodiments, each element of one transducer array is fired sequentially, and all elements of both transducer arrays receive ultrasound scattering data 32. The scanner 130 acquires not only ultrasound propagating from one element to all elements within the same transducer array, but also those ultrasound waves propagating from the emitting element to all elements of the other transducer array, leading to a full 3D ultrasound tomography image of the breast.

Such a UST system 130 allows recording of volumetric ultrasound data, and the image resolution limited by slice thickness will be alleviated. In one eximplary design, the data acquisition electronics 18 allow a maximum of 768 parallel channels, so the number of transducers may be halved per array 132a and 132b. The coarser sampling in the plane of the array will be compensated by the cross illuminations The scanner 130 of FIG. 11 can significantly improve image resolution and quality compared to those obtained from an ultrasound tomography system with one circular transducer array. A 3D ultrasound tomography system 10 of this configuration will be operator independent, which is critical for cancer screening, and will be more cost-effective than an ultrasound tomography system with a cylindrical transducer array.

F. Combination 2D Planar and 2D-Arc Array Scanner

Figure 12:
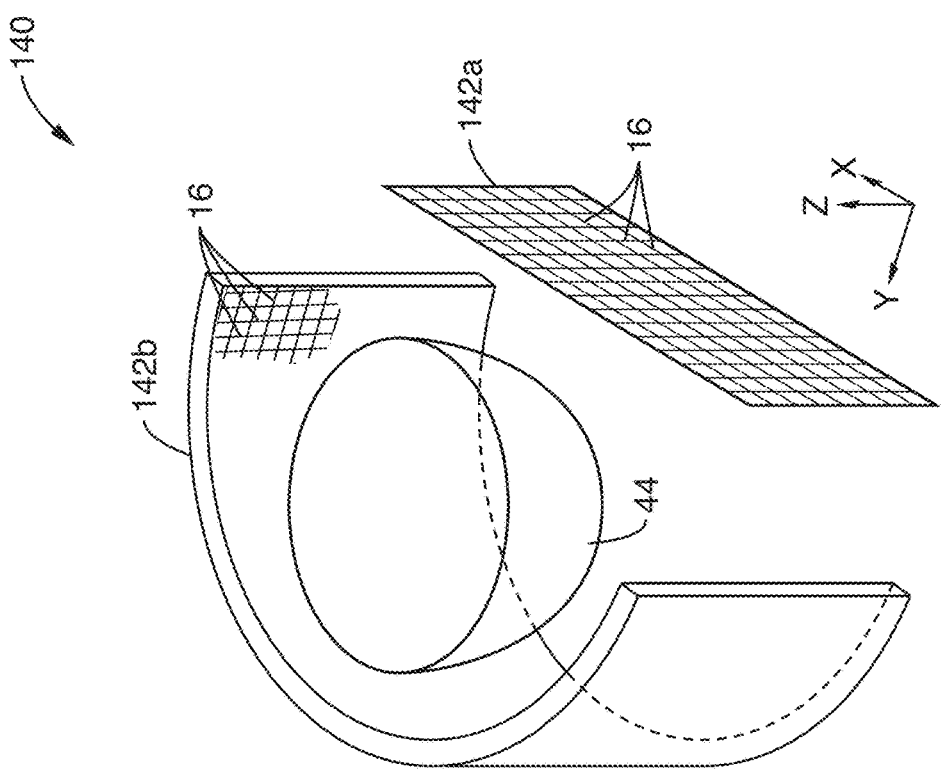
FIG. 12 shows a schematic view of a scanner comprising a semicircular or arcuate array having transducers in an opposing or facing orientation with planar array.

FIG. 12 shows a scanner 140 comprising a semicircular or arcuate array 142b having transducers 16 in an opposing or facing orientation with planar array 142a, with target tissue 44 disposed between the two. The scanner 140 provides a combination of the advantages of the cylindrical transducer array 110 with those of the 2D planner array 100. An ultrasound tomography system 10 with such combination of transducer arrays improves the range of spatial coverage for data acquisition, and the planar array 142 can still be placed near the axillary region.

G. Combination 1D Beam and Arc Array Scanner

Figure 13:
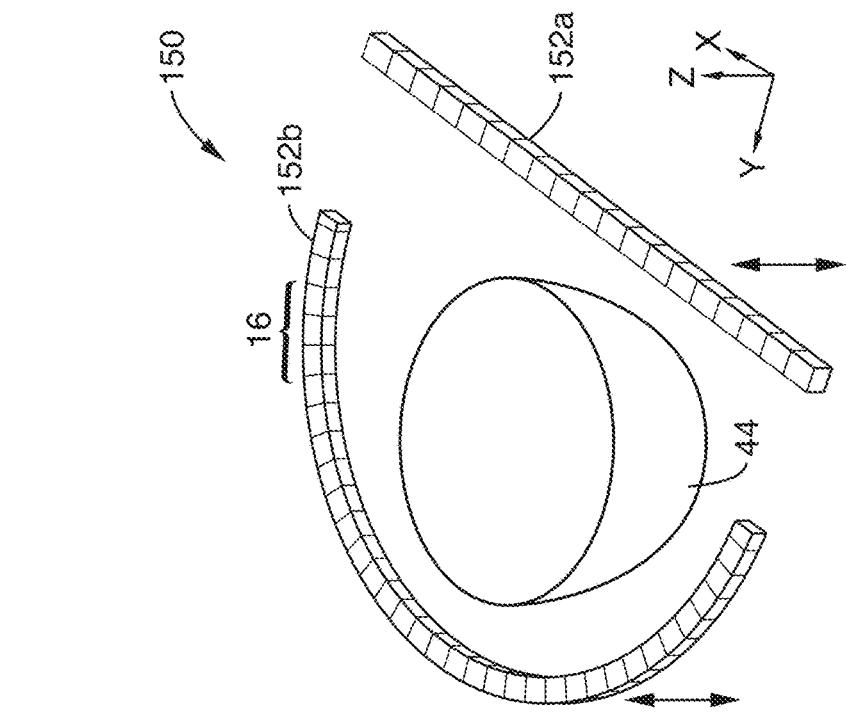
FIG. 13 illustrates a scanner that reduces the 2D arrays in FIG. 12 to 1D arrays.

FIG. 13 illustrates a scanner 150 that reduces the 2D arrays in FIGS. 12 to 1xD arrays (arcuate line array 152b and linear beam array 152a). This configuration, using a one-dimeisional, straight-phased array 152a and a 1D arc-shaped array, 152 reduces the number transducers 16, and thus the number of channels required for data acquisition electronics 18, while improving the spatial coverage of data acquisition compared to when using a two parallel phased transducer array scanner 12 in FIG. 5.

II. Synthetic Aperture Ultrasound Tomography Methods

Figure 14:
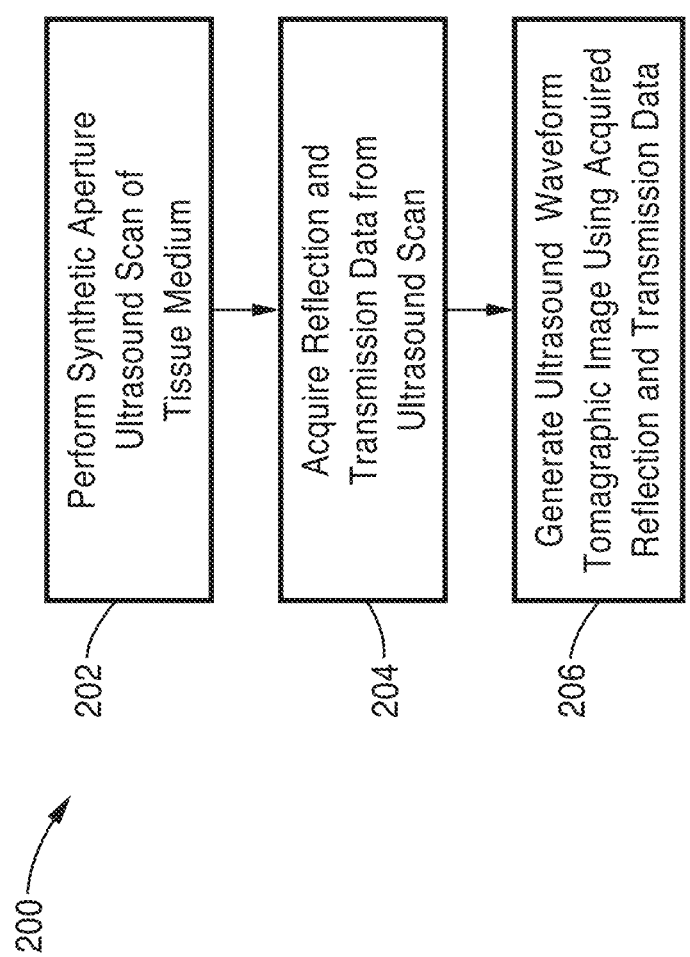
FIG. 14 is a flow diagram of a synthetic aperture ultrasound tomography method in accordance with the present invention.

Referring now to FIG. 14, a flow chart of a synthetic aperture ultrasound tomography method 200 is shown. This method is preferably used with any of the systems and scanners shown in FIG. 1 through FIG. 14, although other scanning systems are contemplated. Ideally, the method is used in conjunction with a scanner that has one or more arrays configured so that a plurality of transducers 16 of an array, or portion of an array, oppose (at a spaced-apart distance across the target scanning medium 44) a plurality of transducers 16 of either another portion of the array, or a separate array, so that reflection and transmission data may be acquired with each successive transducer excitation.

At step 202, the method performs a synthetic aperture ultrasound scan of the tissue medium in accordance with the schematic illustration of scanner 12 FIG. 3. At step 204, reflection and transmission data are simultaneously acquired, as shown in the method 50 of FIG. 4. At step 206, ultrasound waveform tomographic imaging is performed on the acquired reflection and transmission data to generate a high-resolution ultrasound reconstruction image of the target medium 44.

As mentioned previously, a particular shortcoming of existing ultrasound omographic imaging is that they either use only transmission data, or reflection data only, for image reconstructions. In contrast, the synthetic-aperture ultrasound tomography method 200 of the present invention acquired both ultrasound transmission and reflection data at the same time, and use both ultrasound transmission and reflection data for tomographic reconstructions to greatly improve the shapes and quantitative values of mechanical properties of abnormalities.

FIG. 15 through FIG. 18B demonstrate that using numerical breast-phantom data from ultrasound waveform tomography using both transmission and reflection data simultaneously significantly improves the accuracy of tomographic reconstructions, compared to those obtained using only ultrasound transmission data or only ultrasound reflection data.

Numerical phantom data was generated for a synthetic-aperture ultrasound tomography system with a two parallel phased transducer array scanner 12 as shown in FIG. 5. Each transducer array 14a, 15b is comprised of 384 evenly distributed ultrasound transducer elements, with a pitch size of 0.55 mm. The two transducer arrays were separated by 20 cm. The ultrasound source function used is a Ricker wavelet with a central frequency of 1.0 MHz.

Figure 15:
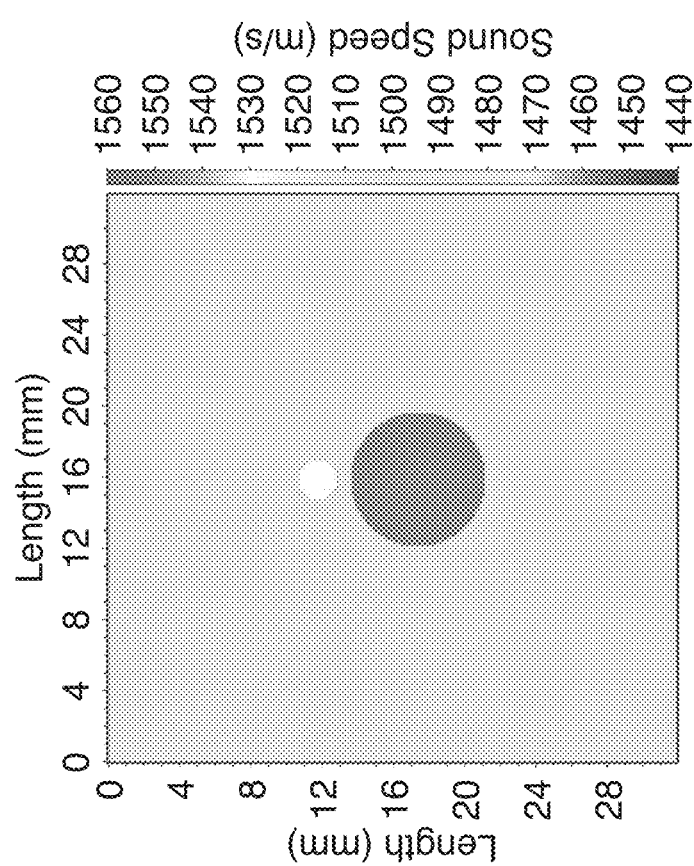
FIG. 15 shows an image of a numerical breast phantom containing two different tumors.

FIG. 15 shows an image of a numerical breast phantom containing two different tumors (small, light tumor, and larger dark tumor). The background sound-speed of the phantom was 1500 m/s, and those of the two tumor speeds were 1530 m/s and 1550 m/s, respectively. The diameters of the tumors were 2.0 mm and 7.0 mm, and approximately 1.3 wavelengths and 4.6 wavelengths. The two tumors were positioned along the longitudinal direction relative to the ultrasound transducer arrays. A high-order finite-difference time-domain wave-equation algorithm in accordance with step 206 was used to compute ultrasound transmission and reflection data.

Figure 16B:
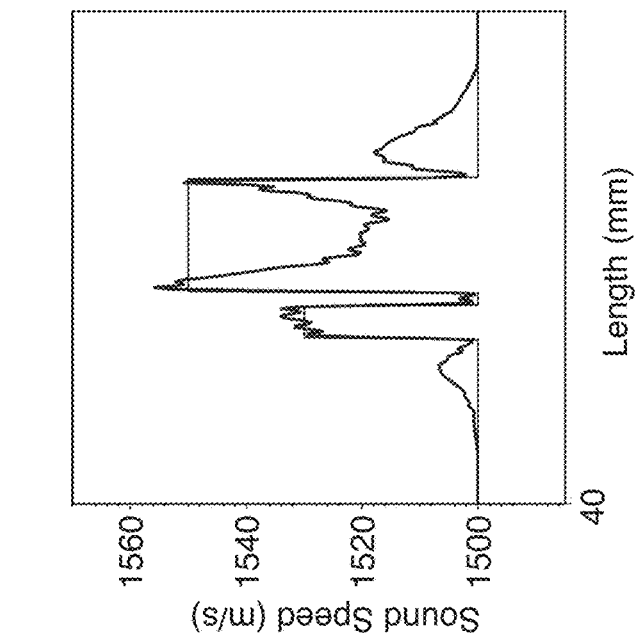
FIG. 16A and FIG. 16B show imaging results (tomographic reconstruction in FIG. 16A, and vertical profile along the center of the tumors in FIG. 16B) obtained using only the reflection data.
Figure 16A:
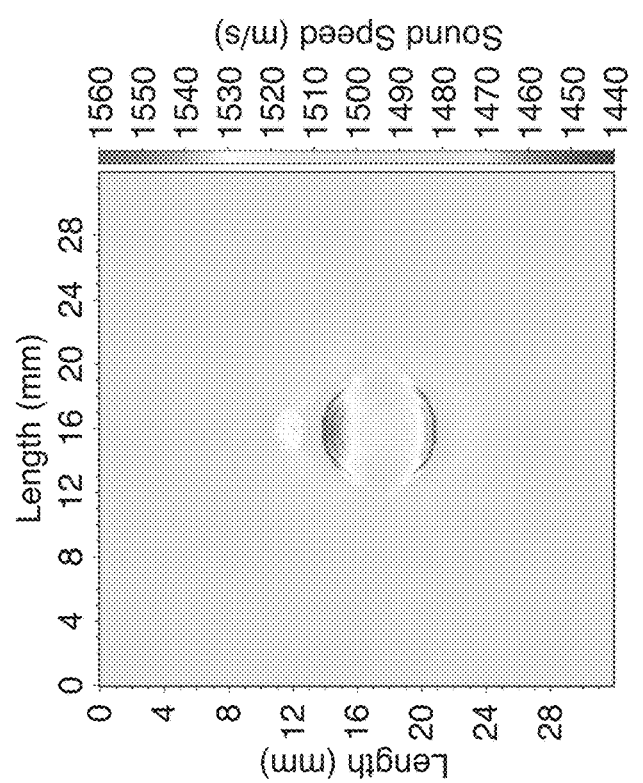
Figure 17B:
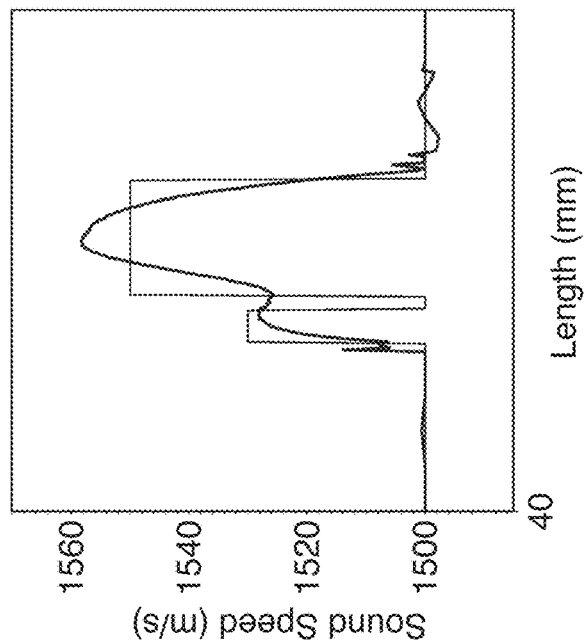
FIG. 17A and FIG. 17B show imaging results (tomographic reconstruction in FIG. 17A, and vertical profile along the center of the tumors in FIG. 17B) obtained using only the transmission data.
Figure 17A:
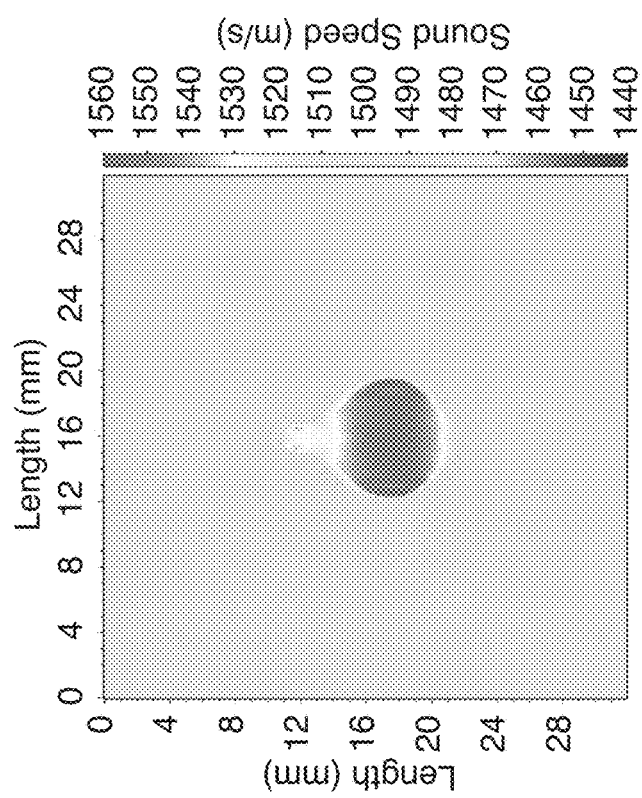

FIG. 16A and FIG. 16B show imaging results (tomographic reconstruction in FIG. 16A, and vertical profile along the center of the tumors in FIG. 16B) obtained using only the reflection data. FIG. 17A and FIG. 17B show imaging results (tomographic reconstruction in FIG. 17A, and vertical profile along the center of the tumors in FIG. 17B) obtained using only the transmission data. FIG. 18A and FIG. 18B show imaging results (tomographic reconstruction in FIG. 18A, and vertical profile along the center of the tumors in FIG. 18B) obtained using both transmission and reflection data simultaneously in accordance with method 200.

The waveform tomographic reconstruction using only the reflection data (FIG. 16A and FIG. 16B) provides mostly edge information of the tumors, and can distinguish the two tumors.

On the other hand, the waveform tomographic reconstruction (FIG. 17A and FIG. 17B) using only the transmission data gives mostly low spatial-wavenumber components of the tumors, and it is almost impossible to separate the two tumors.

By contrast, the waveform tomographic reconstruction using both the transmission and reflection data simultaneously (FIG. 18A and FIG. 18B) takes the advantages of the above two kinds of tomographic reconstructions, and produces an image with much improved tumor edges and sound-speed reconstructions.

A. Synthetic Aperture Ultrasound with Waveform Tomography Inversion

FIG. 19 illustrates a preferred method 206 for generating the ultrasound waveform step of method 200 (FIG. 14) using both transmission and reflection data for ultrasound waveform tomography. As shown in FIG. 19, reflection and transmission data are input at step 210, and ray approximation is performed at step 212 to generate an initial model. Next at step 214, image reconstruction is performed by computing the wave acoustic wave properties of the data by calculating the mean square difference between the observed and synthetic waveforms. In particular, step 214 is performed by performing iterative waveform inversion with regularization, as will be explained in further detail below. From a more basic level, performing step 214 is achieved by solving the acoustic wave equation of Eq. 1 with the minimization model of Eq. 2, described in more detail below.

The acoustic-wave equation in the time domain is given by:

$$\left[\frac{1}{K(r)}\frac{\partial^2}{\partial t^2} - \nabla \cdot \left(\frac{1}{\rho(r)}\nabla\right)\right]p(r, t) = s(t)\delta(r - r_0), \quad \text{Eq. 1}$$

where $\rho(r)$ is the density, $K(r)$ is the bulk modulus, $s(t)$ is the source term, $r_0$ is the source location, and $p(r,t)$ is the pressure field.

The inverse problem of Eq. 1, or waveform tomography, can be posed as a minimization problem such that:

$$E(m) = \min_m \sum_{s=1}^{N_s} \int [d_s(t) - p_s(m, t)]^2 dt, \quad \text{Eq. 2}$$

where $E(m)$ is the misfit function, d represents recorded waveforms, which can be either reflection data, or transmission data, or combined reflection and transmission data, s is the source index, $N_s$ is the number of sources, and m is the model parameter.

The minimization operation in Eq. 2 is to find a model m that yields the minimum difference between observed and synthetic waveforms. The model parameter m is given by:

$$m = \begin{bmatrix} V \text{ or } K \\ \rho \end{bmatrix}, \quad \text{Eq. 3}$$

where $V=\sqrt{K/\rho}$ is the acoustic wave-speed.

A typical approach to minimize the misfit function is the gradient-based method, e.g. the steepest descend or the conjugate gradient methods (NCG). In each step, the model first evaluates the gradient of the misfit function at the current model, and then determines a search direction based on the current gradient or previous gradients. The search direction for the misfit function of acoustic wave is written as:

$$\gamma_k \sim \sum_{s=1}^{N_s} \int_t u_s(x, t; m_k) b_s(x, t; m_k) dt, \quad \text{Eq. 4}$$

where $\gamma$ is the search direction, k the iteration number, u the forward propagated wavefield, b the backward propagated wavefield, x the spatial variable, t the temporal variable. The step length is preferably found by a line search method. The model is updated along the search direction using the step length:

$$m_{k+1} = m_k + \alpha \gamma_k,  \quad \text{Eq. 5}$$

where $\alpha$ is the step length. This process is repeated iteratively until a certain convergence criterion is satisfied.

Although the resolve power of ultrasound waveform tomography is appealing, it is computationally expensive. The computational cost increases linearly with the number of sources, because the search direction $\gamma$ and the step length $\alpha$ are both needed to be evaluated from every source, as shown in Eq. 4 and Eq. 5. As the number of sources increases, ultrasound waveform tomography becomes very time-consuming, particularly for synthetic-aperture ultrasound tomography, where the system usually consists of hundreds to thousands of transducer elements.

The following description details two methods for increasing efficiency in computations for ultrasound waveform tomography. First, the source encoding method of the present invention will be discussed. Then, the data blending method of the present invention will be discussed.

i. Ultrasound Waveform Tomography with Source Encoding

For source encoding, the misfit function may be modified according to:

$$E'(m) = \min_m \sum_{g=1}^{N_g} \int \left\{ \sum_{s=1}^{n_g} [d_{g,s}(t) - p_{g,s}(m,t)] \right\}^2 dt, \quad \text{Eq. 6}$$

where $d_{g,s}$ and $p_{g,s}$ are respectively data and simulated waveforms for the $s^{th}$ source within the $g^{th}$ encoding group, $N_g$ is the number of groups, and $n_g$ is the number of sources encoded in the $g^{th}$ group such that $$N_s = \sum_{g=1}^{N_g} n_g.$$

The misfit function in Eq. 6 can be calculated in only one simulation, because of the linearity of the acoustic wave equation. However, Eq. 6 is not equivalent to Eq. 2, because Eq. 6 contains the cross-terms of different sources, which can be seen by simply expanding Eq. 6.

The source encoding technique of the present invention is used to reduce the cross-terms used in waveform tomography. Referring to FIG. 20, the source encoding method 220 assigns every source (e.g. transducers 16 in FIG. 1) with a phase as a source signature (step 224), and launches multiple sources simultaneously in a single simulation (step 226). The search direction may then be calculated via Eq. 4 using the encoded sources (step 228).

In a preferred embodiment, the number of sources is first divided into groups at step 222, such that a partial search direction is calculated at step 228, and the search directions of all groups are summed at step 230.

In a preferred embodiment, the phases were randomly selected at step 224.

Source encoding method 220 is preferably applied to ultrasound waveform tomography using both transmission and reflection data from a synthetic-aperture ultrasound tomography system (e.g. any of the systems embodied in FIGS. 1-14 above). However, it is appreciated that this method may be applied to any systems and data, whether the data is transmission only or reflection only.

Accordingly, the misfit function is given by:

$$E'(m) = \min_m \sum_{s=1}^{N_s} \int [\bar{d}_s - \bar{p}_s]^2 dt + \quad \text{Eq. 7}$$

$$\sum_{g=1}^{N_g} \sum_{s=1}^{n_g} \sum_{s'=1, s' \neq s}^{n_g} \int [\bar{d}_{g,s} - \bar{p}_{g,s}][\bar{d}_{g,s'} - \bar{p}_{g,s'}] dt.$$

where $\bar{p}$ is the encoded synthetic waveform, and $\bar{d}$ is the encoded data, which may be either transmission data, reflection data, or combined reflection and transmission data.

Eq. 7 and Eq. 2 are equivalent if the cross-term in Eq. 7 can be removed. The encoded waveform and data are given by:

$$\bar{d}_{g,s} = d_{g,s} \times \psi_{g,s},$$

$$\bar{p}_{g,s} = p_{g,s} \times \psi_{g,s}, \quad \text{Eq. 8}$$

where $\psi$ is a random phase or phase value. In a method of performing waveform tomography inversion according to the present invention, this phase value is added to the source and data during numerical simulations of forward wave propagation from sources and backward propagation of ultrasound wavefields from receivers.

Algorithm 1 below shows an implementation ultrasound waveform tomography in accordance with the source encoding 220 shown in FIG. 20, where TOL is the input tolerance for the iteration, and $m^{(0)}$ is the input model.

---
Algorithm 1 Ultrasound waveform
tomography using source encoding
---

Input: $m^{(0)}$, TOL
Output: $m^{(k)}$
 1: Separate $N_s$ sources into $N_g$ groups (step 222)
 2: Initialize k = 0, $\gamma_0$ ;
 3: while { $\|\gamma_k\|$ > TOL } do
 4:   for g =1, $N_g$
 5:     Apply a random phase to each source and corresponding data within $g^{th}$ group (step 224);
 6:     Start all the sources within $g^{th}$ group (step 226)
 7:     Calculate partial search direction (Eq. 4) using the encoded sources and data in $g^{th}$ group ;
 8:   end do
 9:   Sum up the partial search directions of all the groups to obtain $\gamma_k$ (step 230);
10: Update model $m^{(k)}$ (Eq.5) ;
11: k ← k + 1 ;
12: end while ii. Ultrasound Waveform Tomography with Data Blending For data blending, the misfit function may be modified according to:

$$E'(m) = \min_m \sum_{g=1}^{N_g} \int \left\{ \sum_{s=1}^{n_g} [d_{g,s}(t) - p_{g,s}(m,t)] \right\}^2 dt, \quad \text{Eq. 9}$$

where $d_{g,s}$ and $p_{g,s}$ are respectively data and simulated waveforms for the $s^{th}$ source within the $g^{th}$ blending group, $N_g$ is the number of groups, and $n_g$ is the number of sources blended in the $g^{th}$ group such that $$N_s = \sum_{g=1}^{N_g} n_g.$$

The misfit function in Eq. 6 can be calculated in only one simulation, because of the linearity of the acoustic wave equation. However, the Eq. 6 is not equivalent to Eq. 2, because Eq. 6 contains the cross-terms of different sources, which can be seen by simply expanding Eq. 6.

Figure 21:
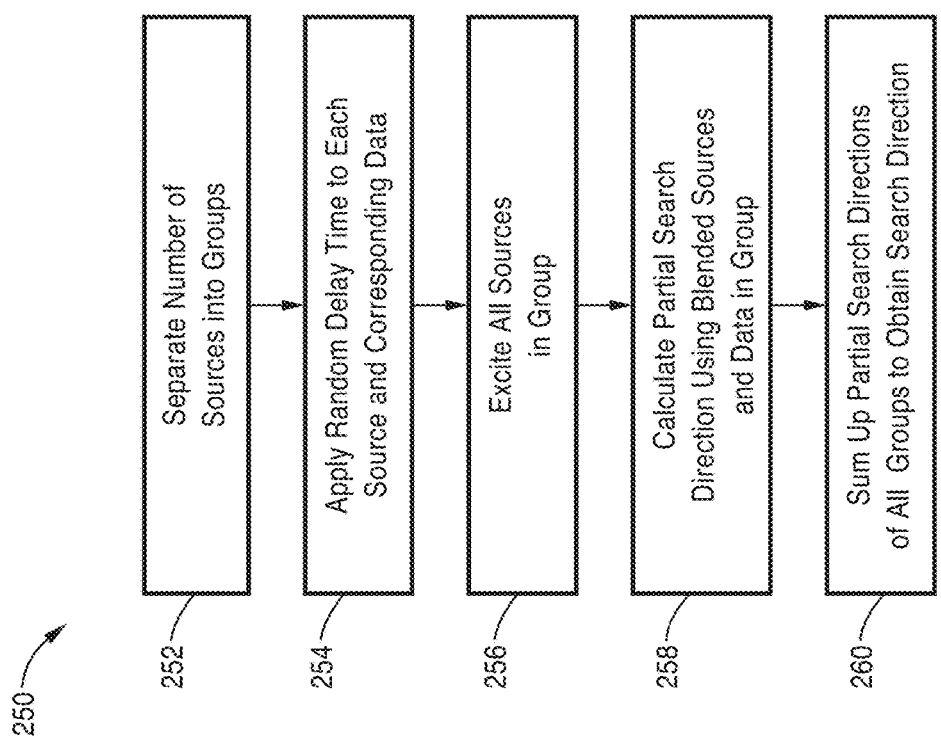
FIG. 21 illustrates a flow diagram of a data blending method for ultrasound waveform tomography in accordance with the present invention.

The data blending technique of the present invention is used to reduce the cross-terms used in waveform tomography. Referring to FIG. 21, the data blending method 250 applies a random delay time to each source (e.g. transducers 16 in FIG. 1) and corresponding data (step 254), and launches or excites multiple sources simultaneously in a single simulation (step 256). The search direction may then be calculated via Eq. 4 using the blended sources (step 258).

In a preferred embodiment, the number of sources is first divided into groups at step 252, such that a partial search direction is calculated at step 258, and the search directions of all groups are summed at step 260.

In a preferred embodiment, the phases were randomly selected at step 254.

Data blending method 250 is preferably applied to ultrasound waveform tomography using both transmission and reflection data from a synthetic-aperture ultrasound tomography system (e.g. any of the systems embodied in FIG. 1 through FIG. 14 above). However, it is appreciated that this method may be applied to any systems and data, whether the data is transmission only or reflection only.

Accordingly, the misfit function is given by:

$$E'(m) = \min_m \sum_{s=1}^{N_s} \int [d_s(t) - p_s(m,t)]^2 dt + \qquad \text{Eq. 10}$$

$$\sum_{g=1}^{N_g} \sum_{s=1}^{n_g} \sum_{s'=1,s'\neq s}^{n_g} \int [d_{g,s}(t) - p_{g,s}(m,t)][d_{g,s'}(t) - p_{g,s'}(m,t)] dt.$$

where p is the encoded synthetic waveform, and d is the encoded data, which may be either transmission data, reflection data, or combined reflection and transmission data.

During simulations in inversion, we add a random time delay $t_s$ to each common-transmitter dataset and the corresponding forward propagation wavefield from the transmitting transducer element (source), so we have:

$$\bar{d}_{g,s}(t) = \int d_{g,s}(\omega) e^{i\omega(t+t_{g,s})} d\omega,$$

$$\bar{p}_{g,s}(t) = \int p_{g,s}(\omega) e^{i\omega(t+t_{g,s})} d\omega, \qquad (11)$$

where $\omega$ is the frequency, $t_{g,s}$ is the delay time for source s within the $g^{th}$ group. In a method of performing waveform tomography inversion according to the present invention, this time delay is added to the source and data during numerical simulations of forward wave propagation from sources and backward propagation of ultrasound wavefields from receivers.

In the frequency domain, dropping all the variables, E and E' with blended sources can be written as:

$$E(m) = \min_m \left\{ \sum_{s=1}^{N_s} [d_s - p_s][d_s - p_s]^* d\omega \right\}, \qquad \text{Eq. 12}$$

and $$E'(m) = \min_m \sum_{s=1}^{N_s} \int [\bar{d}_s - \bar{p}_s][\bar{d}_s - \bar{p}_s]^* d\omega + \qquad \text{Eq. 13}$$

$$\sum_{g=1}^{N_g} \sum_{s=1}^{n_g} \sum_{s'=1,s'\neq s}^{n_g} \int [\bar{d}_{g,s} - \bar{p}_{g,s}][\bar{d}_{g,s'} - \bar{p}_{g,s'}]^* d\omega.$$

Substituting Eq. 10 into Eq. 8, we get:

$$E'(m) = E(m) + \qquad \text{Eq. 14}$$

$$\sum_{g=1}^{N_g} \sum_{s=1}^{n_g} \sum_{s'=1,s'\neq s}^{n_g} \int [d_{g,s} - p_{g,s}][d_{g,s'} - p_{g,s'}]^* e^{i\omega(t_{g,s} - t_{g,s'})} d\omega.$$

Generally, the second term in Eq. 14 does not vanish. If we choose $t_s$ and $t_{s'}$ randomly, the first term in equation Eq. 14 is not affected, but the second term changes in each iteration step. As the number of iterations increases, the influence of the first term in the reconstruction accumulates, while the influence of the second term gradually reduces.

Algorithm 2 below shows an implementation ultrasound waveform tomography in accordance with the source encoding 250 shown in FIG. 21, where TOL is the input tolerance for the iteration, and $m^{(0)}$ is the input model.

---

Algorithm 2 Ultrasound waveform tomography using data blending

Input: $m^{(0)}$, TOL
Output: $m^{(k)}$
1: Separate $N_s$ sources and the corresponding data into $N_g$ groups (step 252)
2: Initialize k = 0, $\gamma_0$;
3: while { $\|\gamma_k\|$ > TOL } do
4:   for g =1, $N_g$
5:     Apply a random delay-time to each source (step 254) and corresponding data within $g^{th}$ group;
6:     Start all the sources within $g^{th}$ group (step 256);
7:     Calculate partial search direction using the blended sources and data in $g^{th}$ group (step 258);
8:     end do
9:     Sum up the partial search directions of all the groups to obtain $\gamma_k$ (step 260);
10:    Update model $m^{(k)}$ (Eq. 5);
11:    k ← k + 1;
12: end while

---

Tests were conducted to evaluate the source encoding method 220 (FIG. 20) and the data blending method 250 (FIG. 21) of the present invention.

Figure 22:
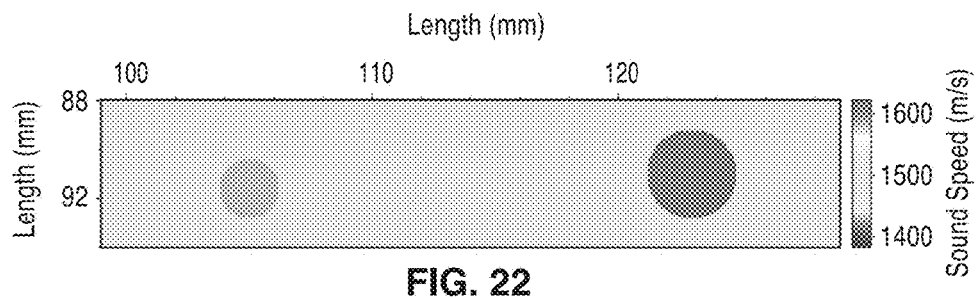
FIG. 22 shows an image of two small tumors in the numerical breast phantom scanned using the synthetic-aperture ultrasound tomography system similar to that shown in FIG. 1.

To validate the source encoding method 220 for ultrasound waveform tomography a numerical breast phantom was scanned using a synthetic-aperture ultrasound tomography system with two parallel phased transducer arrays similar to the scanner configuration 12 of FIG. 5. The numerical breast phantom contained two breast tumors located near the center of the imaging region, as shown in FIG. 22. One of the tumors has a diameter of 2.2 mm, the other has a diameter of 3.3 mm. The breast tumors are positioned along the transverse direction relative to the transducer arrays.

The waveform inversion result for ultrasound waveform tomography of transmission and reflection data without using source encoding is shown in FIG. 23A and FIG. 23B. The location and the sound speed of the two small tumors are fully reconstructed. FIG. 23A and FIG. 23B are used as a reference to compare with the results obtained using ultrasound waveform tomography with source encoding.

In one simulation, 4, 8, 12, and 24 sources were encoded. Therefore, the computational times are one forth, one eighth, one twelfth and one twenty-fourth of that for the original ultrasound waveform tomography. The inversion results of the four different groupings after 20 iterations are almost identical, as shown in FIG. 24A through FIG. 24D.

The horizontal profiles of FIG. 24A through FIG. 24D at the vertical location of 91 mm also show that the four different groupings give similar reconstruction results. The boundary of the larger tumor on the right is a little blurred when using 24 sources in one simulation (see the horizontal locations at 120 mm and 122 mm in FIG. 25A through FIG. 25D).

Combining encoded data from multiple sources in one simulation results in a few image artifacts, as can be seen in FIG. 24A through FIG. 24D and FIG. 25A through FIG. 25D.

Ultrasound waveform tomography with source encoding not only produces almost the same reconstruction results as the original ultrasound waveform tomography, but also keeps the convergence rate unchanged.

The results at the third iteration of the four different groupings explain the process during inversion (see FIG. 26A through FIG. 26D). Again, the profiles in FIG. 26A through FIG. 26D are similar to one another. More encoded sources used in one simulation only produce slightly more image noise than those obtained using fewer encoded sources (from 114 mm to 119 mm in FIG. 6). The image noise is weaker at the locations where the tumors present (from 111 mm to 113 mm in FIG. 6). This implies that the source encoding successfully eliminates the interference among different sources in one simulation. After many iteration steps, the artifact caused by the cross-interference among different sources is further reduced (FIG. 25A through FIG. 25D).

To validate the data blending method 250 for ultrasound waveform tomography, a numerical breast phantom was scanned using a synthetic-aperture ultrasound tomography system with two parallel phased transducer arrays similar to the scanner configuration 12 of FIG. 5. The imaging region had a length of 211 mm and a width of 200 mm. 384 transducer elements were placed along the two parallel transducer arrays. The central frequency of ultrasound was 1 MHz. The phantom had a background sound speed of 1500 m/s.

The numerical breast phantom contained two breast tumors located near the center of the imaging region, as shown in FIG. 27. One of the tumors has a diameter of 2.2 mm, the other has a diameter of 3.3 mm. The breast tumors are positioned along the transverse direction relative to the transducer arrays.

The waveform inversion result for ultrasound waveform tomography of transmission and reflection data without using source encoding is shown in FIG. 28A and FIG. 28B. The location and the sound speed of the two small tumors are fully reconstructed. FIG. 28A and FIG. 28B are used as a reference to compare with the results obtained using ultrasound waveform tomography with source encoding.

In one simulation, synthetic-aperture ultrasound data from 4, 8, and 24 sources in were blended. The computational times of ultrasound waveform tomography with blending data are about one forth, one eighth, one twelfth and one twenty-fourth of that for the original ultrasound waveform tomography without data blending. We used three different maximum delay times in our numerical examples: one period, ½ periods and ¼ periods, to study the effect of the maximum time delay used in blended data.

The ultrasound waveform tomography results of the three different data-blending schemes with three different maximum delay times after 20 iterations are almost identical (FIG. 29A through FIG. 29C). Using multiple sources in one simulation leads to only a few image artifacts compared with the result obtained using the original waveform tomography without data blending (FIG. 28A and FIG. 28B). These image artifacts are seen more clearly from the horizontal profiles in FIG. 30A through FIG. 30C, FIG. 32A through FIG. 32C, and FIG. 34A through FIG. 34C, which correspond to the waveform tomography results of FIG. 29A through FIG. 29C, FIG. 31A through FIG. 31C, and FIG. 33A through FIG. 33C.

When using the same maximum delay time, more sources are blended together, the stronger the artifacts, especially within the larger tumor (see the horizontal locations at 120 mm and 122 mm in FIG. 30A through FIG. 30C, FIG. 32A through FIG. 32C, and FIG. 34A through FIG. 34C).

When the maximum delay time decreases, the artifacts generally increase. The effects are observed more clearly when more sources are blended together (see FIG. 30C, FIG. 32C, and FIG. 34C). If fewer sources are blended together, decreasing the maximum delay time does not change the reconstruction result significantly (see FIG. 30A, FIG. 32A, and FIG. 34A). This result suggests that a longer delay time needs to be used when data from more sources are blended together.

The data blending in ultrasound waveform tomography not only results in tomography results as good as that of the original ultrasound waveform inversion, but also keeps the convergence rate unchanged. The convergence rates in our numerical examples of ultrasound waveform tomography with blending data are the same as that of the original waveform tomography without data blending. This suggests that the data blending approach is very efficient to reduce the interference between different sources within a few iteration steps. Therefore, data blending serves as a powerful tool to significantly reduce the computational cost of ultrasound waveform tomography.

Ultrasound waveform tomography methods using source encoding and data blending were generated, and both validated the method using ultrasound transmission and reflection data from a synthetic-aperture ultrasound tomography systems. The results show that the source encoding and data blending both dramatically improve the computational efficiency of ultrasound waveform inversion by simulating the wavefields of multiple sources at the same time during inversion. The computational cost is one to two orders of magnitudes less than that for the original waveform tomography.

The source encoding technique significantly reduces the cross-interference among different sources in one simulation by assigning a random phase signature to every source and its common-source data. The reconstructed image obtained using the source encoding is almost identical to that obtained using the original waveform tomography. Meanwhile, the convergence rate of ultrasound waveform tomography with source encoding is unchanged from the original ultrasound waveform tomography. Our numerical examples show that ultrasound waveform tomography with source encoding is feasible for future clinical applications.

In summary, the synthetic-aperture ultrasound tomography systems and methods of the present invention acquire ultrasound transmission and reflection data at the same time, and we have demonstrated that ultrasound waveform tomography using either source endocing or data blending greatly improves computational efficiency, leading to a reduced computation cost that is less than one tenth of the computational cost for the original ultrasound waveform tomography.

From the discussion above it will be appreciated that the invention can be embodied in various ways, including the following:

1. An ultrasound tomography imaging method for imaging a tissue medium with one or more ultrasound transducer arrays comprising a plurality of transducers, wherein said transducers comprise source transducers, receiving transducers, or both, the method comprising: assigning a phase value to the plurality of source transducers; exciting the plurality of transducers; and calculating a search direction based on data relating to the excited plurality of transducers.

2. A method as recited in any of the preceding embodiments, wherein the phase value is randomly assigned.

3. A method as recited in any of the preceding embodiments, wherein said phase value functions a source signature between different source transducers.

4. A method as recited in any of the preceding embodiments, wherein said phase value reduces cross interference produced by different source transducers.

5. A method as recited in any of the preceding embodiments, further comprising: performing numerical waveform inversion to generate an ultrasound waveform tomography image reconstruction; wherein said phase values are assigned during the numerical waveform inversion.

6. A method as recited in any of the preceding embodiments, wherein the image reconstruction comprises calculating forward wavefield propagation from transducer sources and backward wavefield propagation of from ultrasound receivers.

7. A method as recited in any of the preceding embodiments, wherein the image reconstruction further comprises: exciting a first transducer within plurality of transducers to generate an ultrasound field within the tissue medium; acquiring a transmission signal and a reflection signal from a second transducer within the one or more ultrasound transducer arrays; and generating an ultrasound waveform tomography image reconstruction using both the acquired reflection and transmission signals.

8. A method as recited in any of the preceding embodiments, wherein said image reconstruction is a function of computing an acoustic wave property of the reflection and transmission signals by calculating a minimum mean square difference between observed and synthetic waveforms relating to the reflection and transmission signals.

9. A method as recited in any of the preceding embodiments, wherein said image reconstruction is a function of:

$$E(m) = \min_{m} \sum_{s=1}^{N_s} \int [d_s(t) - p_s(m, t)]^2 dt,$$

where E(m) is the misfit function, d is recorded waveforms, s is the source index, $N_s$ is the number of sources, and m is the model parameter.

10. A method as recited in any of the preceding embodiments, wherein the recorded waveforms comprise either reflection data or transmission data from the transducers.

11. A method as recited in any of the preceding embodiments, wherein the recorded waveforms comprise reflection and transmission data from the transducers.

12. A method as recited in any of the preceding embodiments, wherein the search direction is used in calculating a gradient of the misfit function.

13. A method as recited in any of the preceding embodiments, wherein the search direction is calculated according to:

$$\gamma_k \sim \sum_{s=1}^{N_s} \int_t u_s(x, t; m_k) b_s(x, t; m_k) dt,$$

where γ is the search direction, k the iteration number, u is a forward propagated wavefield, b is a backward propagated wavefield, x is a spatial variable, and t is a temporal variable.

14. An ultrasound tomography imaging system for imaging a tissue medium with one or more ultrasound transducer arrays comprising a plurality of transducers, wherein said transducers comprise source transducers, receiving transducers, or both, said the system comprising: a processor; and programming executable on said processor and configured for: assigning a phase value to the plurality of source transducers; exciting the plurality of transducers; and calculating a search direction based on data relating to the excited plurality of transducers.

15. A system as recited in any of the preceding embodiments, wherein the phase value is randomly assigned.

16. A system as recited in any of the preceding embodiments, phase value functions a source signature between different source transducers.

17. A system as recited in any of the preceding embodiments, wherein said phase value reduces cross interference produced by different source transducers.

18. A system as recited in any of the preceding embodiments: wherein said programming is further configured for performing numerical waveform inversion to generate an ultrasound waveform tomography image reconstruction; wherein said phase values are assigned during the numerical waveform inversion.

19. A system as recited in any of the preceding embodiments, wherein the image reconstruction comprises calculating forward wavefield propagation from transducer sources and backward wavefield propagation of from ultrasound receivers.

20. A system as recited in any of the preceding embodiments, wherein the image reconstruction further comprises: exciting a first transducer within plurality of transducers to generate an ultrasound field within the tissue medium; acquiring a transmission signal and a reflection signal from a second transducer within the one or more ultrasound transducer arrays; and generating an ultrasound waveform tomography image reconstruction using both the acquired reflection and transmission signals.

21. A system as recited in any of the preceding embodiments, wherein said image reconstruction is a function of computing an acoustic wave property of the reflection and transmission signals by calculating a minimum mean square difference between observed and synthetic waveforms relating to the reflection and transmission signals.

22. A system as recited in any of the preceding embodiments, wherein said image reconstruction is a function of:

$$E(m) = \min_{m} \sum_{s=1}^{N_s} \int [d_s(t) - p_s(m, t)]^2 dt,$$

where E(m) is the misfit function, d is recorded waveforms, s is the source index, $N_s$ is the number of sources, and m is the model parameter.

23. A system as recited in any of the preceding embodiments, wherein the recorded waveforms comprise either reflection data or transmission data from the transducers.

24. A system as recited in any of the preceding embodiments, wherein the recorded waveforms comprise reflection and transmission data from the transducers.

25. A system as recited in any of the preceding embodiments, wherein the search direction is used in calculating a gradient of the misfit function.

26. A system as recited in any of the preceding embodiments, wherein the search direction is calculated according to:

$$\gamma_k \sim \sum_{s=1}^{N_s} \int_t u_s(x, t; m_k) b_s(x, t; m_k) dt,$$

where $\gamma$ is the search direction, k the iteration number, u the forward propagated wavefield, b the backward propagated wavefield, x the spatial variable, t the temporal variable.

27. An ultrasound tomography imaging method for imaging a tissue medium with one or more ultrasound transducer arrays comprising a plurality of transducers, wherein said transducers comprise source transducers, receiving transducers, or both, the method comprising: assigning a time delay to the plurality of source transducers; exciting the plurality of transducers; and calculating a search direction based on data relating to the excited plurality of transducers.

28. A method as recited in any of the preceding embodiments, wherein the time delay is randomly assigned.

29. A method as recited in any of the preceding embodiments, wherein the time delay functions a source signature between different source transducers.

30. A method as recited in any of the preceding embodiments, wherein the time delay reduces cross interference produced by different source transducers.

31. A method as recited in any of the preceding embodiments, further comprising: performing numerical waveform inversion to generate an ultrasound waveform tomography image reconstruction; wherein said phase values are assigned during the numerical waveform inversion.

32. A method as recited in any of the preceding embodiments, wherein the image reconstruction comprises calculating forward wavefield propagation from transducer sources and backward wavefield propagation of from ultrasound receivers.

33. A method as recited in any of the preceding embodiments, wherein the image reconstruction further comprises: exciting a first transducer within plurality of transducers to generate an ultrasound field within the tissue medium; acquiring a transmission signal and a reflection signal from a second transducer within the one or more ultrasound transducer arrays; and generating an ultrasound waveform tomography image reconstruction using both the acquired reflection and transmission signals.

34. A method as recited in any of the preceding embodiments, wherein said image reconstruction is a function of computing an acoustic wave property of the reflection and transmission signals by calculating a minimum mean square difference between observed and synthetic waveforms relating to the reflection and transmission signals.

35. A method as recited in any of the preceding embodiments, wherein said image reconstruction is a function of:

$$E(m) = \min_m \sum_{s=1}^{N_s} \int [d_s(t) - p_s(m, t)]^2 dt,$$

where E(m) is the misfit function, d is recorded waveforms, s is the source index, $N_s$ is the number of sources, and m is the model parameter.

36. A method as recited in any of the preceding embodiments, wherein the recorded waveforms comprise either reflection data or transmission data from the transducers.

37. A method as recited in any of the preceding embodiments, wherein the recorded waveforms comprise reflection and transmission data from the transducers.

38. A method as recited in any of the preceding embodiments, wherein the search direction is used in calculating a gradient of the misfit function.

39. A method as recited in any of the preceding embodiments, wherein the search direction is calculated according to:

$$\gamma_k \sim \sum_{s=1}^{N_s} \int_t u_s(x, t; m_k) b_s(x, t; m_k) dt,$$

where $\gamma$ is the search direction, k the iteration number, u is a forward propagated wavefield, b is a backward propagated wavefield, x is a spatial variable, and t is a temporal variable.

40. An ultrasound tomography imaging system for imaging a tissue medium with one or more ultrasound transducer arrays comprising a plurality of transducers, wherein said transducers comprise source transducers, receiving transducers, or both, the system comprising: a processor; and programming executable on said processor and configured for: assigning a time delay to the plurality of source transducers; exciting the plurality of transducers; and calculating a search direction based on data relating to the excited plurality of transducers.

41. A system as recited in any of the preceding embodiments, wherein the time delay is randomly assigned.

42. A system as recited in any of the preceding embodiments, wherein the time delay functions a source signature between different source transducers.

43. A system as recited in any of the preceding embodiments, wherein the time delay reduces cross interference produced by different source transducers.

44. A system as recited in any of the preceding embodiments: wherein said programming is further configured for performing numerical waveform inversion to generate an ultrasound waveform tomography image reconstruction; wherein said phase values are assigned during the numerical waveform inversion.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic.

As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula (e), or computational depiction(s).

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An ultrasound tomography imaging method for imaging a tissue medium utilizing a synthetic-aperture ultrasound tomography system comprising two or more ultrasound transducer arrays, spaced apart from each other, each comprising a plurality of transducers, wherein said transducers comprise source transducers, receiving transducers, or both, the method comprising:
   assigning a different phase value to each of at least three source transducers of the plurality of source transducers of the synthetic-aperture ultrasound tomography system;
   exciting the at least three source transducers of the two or more ultrasound transducer arrays of the synthetic-aperture ultrasound tomography system in accordance with the assigned different phase values to generate a plurality of ultrasound waveforms in the tissue medium;
   receiving data from the receiving transducers in accordance with transmissions and reflections of the plurality of ultrasound waveforms through the tissue medium;
   performing a numerical simulation of forward propagation of wavefields from the source transducers and backward propagation of wavefields from the receiving transducers based on the data from the receiving transducers;
   calculating a search direction based on the forward propagation of wavefields and the backward propagation of wavefields;
   updating a model based on the search direction; and
   computing an ultrasound waveform tomography image reconstruction in accordance with the updated model.

2. A method as recited in claim 1, wherein the phase value is randomly assigned.

3. A method as recited in claim 2, wherein said phase value functions as a source signature between different ones of the source transducers.

4. A method as recited in claim 2, wherein said phase value reduces cross interference produced by different ones of the source transducers.

5. A method as recited in claim 1, further comprising:
   performing numerical waveform inversion to generate the ultrasound waveform tomography image reconstruction;
   wherein said phase values are assigned during the numerical waveform inversion.

6. A method as recited in claim 5, wherein the image reconstruction comprises calculating forward wavefield propagation from source transducers and backward wavefield propagation from receiving transducers.

7. A method as recited in claim 6, wherein the image reconstruction further comprises:
   receiving a transmission signal and a reflection signal at one of the receiving transducers within the one or more ultrasound transducer arrays; and
   generating an ultrasound waveform tomography image reconstruction using both the acquired reflection and transmission signals.

8. A method as recited in claim 5, wherein said image reconstruction is a function of:

$$E(m) = \min_m \sum_{s=1}^{N_s} \int [d_s(t) - p_s(m, t)]^2 dt,$$

where E(m) is the misfit function, d is one of transmission data and reflection data, s is a source index indicating one of the source transducers, $N_s$ is the number of source transducers, and m is the model parameter.

9. A method as recited in claim 8, wherein the data from the receiving transducers comprise either reflection data or transmission data from the transducers.

10. An ultrasound tomography imaging system for imaging a tissue medium comprising:
    two or more ultrasound transducer arrays, spaced apart from each other, each of the ultrasound transducer arrays comprising a plurality of transducers, the transducers comprising a plurality of source transducers and a plurality of receiving transducers;

a processor; and programming executable on said processor and configured for:

assigning a different phase value to each of at least three source transducers of the plurality of source transducers;

exciting the at least three source transducers of the two or more ultrasound transducer arrays in accordance with the assigned different phase values to generate a plurality of ultrasound waveforms in the tissue medium;

receiving data from the receiving transducers in accordance with transmissions and reflections of the plurality of ultrasound waveforms through the tissue medium;

performing a numerical simulation of forward propagation of wavefields from the source transducers and backward propagation of wavefields from the receiving transducers based on the data from the receiving transducers;

calculating a search direction based on the forward propagation of wavefields and the backward propagation of wavefields;

updating a model based on the search direction; and computing an ultrasound waveform tomography image reconstruction in accordance with the updated model.

11. A system as recited in claim 10, wherein the phase value is randomly assigned.

12. A system as recited in claim 11, phase value functions a source signature between different ones of the source transducers.

13. A system as recited in claim 11, wherein said phase value reduces cross interference produced by different ones of the source transducers.

14. A system as recited in claim 11:

wherein said programming is further configured for performing numerical waveform inversion to generate the ultrasound waveform tomography image reconstruction;

wherein said phase values are assigned during the numerical waveform inversion.

15. A system as recited in claim 14, wherein the image reconstruction comprises calculating forward wavefield propagation from source transducers and backward wavefield propagation from receiving transducers.

16. A system as recited in claim 14, wherein the image reconstruction further comprises:

receiving a transmission signal and a reflection signal at one of the receiving transducers within the one or more ultrasound transducer arrays; and generating an ultrasound waveform tomography image reconstruction using both the acquired reflection and transmission signals.

17. A system as recited in claim 14, wherein said image reconstruction is a function of:

$$E(m) = \min_m \sum_{s=1}^{N_s} \int [d_s(t) - p_s(m, t)]^2 dt,$$

where E(m) is the misfit function, d is one of transmission data and reflection data, s is a source index indicating one of the source transducers, $N_s$ is the number of source transducers, and m is the model parameter.

18. A system as recited in claim 17, wherein the data from the receiving transducers comprise either reflection data or transmission data from the transducers.

* * * * *

UNITED STATES PATENT AND TRADEMARK OFFICE
CERTIFICATE OF CORRECTION

PATENT NO. : 10,034,656 B2
APPLICATION NO. : 14/339770
DATED : July 31, 2018
INVENTOR(S) : Lianjie Huang et al.

It is certified that error appears in the above-identified patent and that said Letters Patent is hereby corrected as shown below:

On the Title Page

| | |
|---|---|
| Page 2, Column 2, item (56), other Publications, Line 7 | Delete "PCT/U52013/024545," and insert -- PCT/US2013/024545, -- |
| Page 2, Column 2, item (56), other Publications, Line 11 | Delete "PCT/U52013/024656," and insert -- PCT/US2013/024656, -- |
| Page 2, Column 2, item (56), other Publications, Line 15 | Delete "PCT/U52013/024662," and insert -- PCT/US2013/024662, -- |
| Page 2, Column 2, item (56), other Publications, Line 34 | Delete "OWLS" and insert -- CWLS -- |

Signed and Sealed this
Seventh Day of July, 2020

Andrei Iancu
*Director of the United States Patent and Trademark Office*